US012558433B2

(12) United States Patent
Laboda et al.

(10) Patent No.: US 12,558,433 B2
(45) Date of Patent: Feb. 24, 2026

(54) POLYNUCLEOTIDE-LINKED BIOCONJUGATES AND METHODS OF MAKING AND USING

(71) Applicant: PHITONEX, Inc., Carlsbad, CA (US)

(72) Inventors: Craig Laboda, Durham, NC (US); Michael Stadnisky, Bend, OR (US); Christopher Dwyer, Chapel Hill, NC (US); Nicholas Pinkin, Durham, NC (US)

(73) Assignee: PHITONEX, Inc., Durham, NC (US)

( * ) Notice: Subject to any disclaimer, the term of this patent is extended or adjusted under 35 U.S.C. 154(b) by 995 days.

(21) Appl. No.: 17/544,608

(22) Filed: Dec. 7, 2021

(65) Prior Publication Data

US 2022/0218841 A1 Jul. 14, 2022

Related U.S. Application Data

(63) Continuation-in-part of application No. PCT/US2020/057247, filed on Oct. 24, 2020.

(Continued)

(51) Int. Cl.
*A61K 47/68* (2017.01)
*A61K 47/54* (2017.01)

(52) U.S. Cl.
CPC ........ *A61K 47/6889* (2017.08); *A61K 47/549* (2017.08)

(58) Field of Classification Search
CPC ............. A61K 47/6889; A61K 47/549; G01N 2458/10; G01N 33/533; G01N 33/582;
(Continued)

(56) References Cited

U.S. PATENT DOCUMENTS 8,309,306 B2    11/2012    Nolan et al.
8,445,412 B2    5/2013    Hirschbein et al.
(Continued)

FOREIGN PATENT DOCUMENTS

CN        109996889 A        7/2019
JP        2011217708 A       11/2011
(Continued)

OTHER PUBLICATIONS

Flor et al., DNA-Directed Assembly of Antibody-Fluorophore Conjugates for Quantitative Multiparametric Flow Cytometry, ChemBioChem, Dec. 2013, 15, 267-275 (Year: 2013).*
(Continued)

*Primary Examiner* — Anne M. Gussow
*Assistant Examiner* — Allison E Schloop
(74) *Attorney, Agent, or Firm* — Klarquist Sparkman, LLP

(57) ABSTRACT

Provided for herein is a polynucleotide-modified bioconjugate comprising a substrate such as an antibody or bead linked to a conjugate component via a nucleic acid linker. Also provided are methods of making and using such bioconjugates. Conjugation methods for creating the bioconjugate are stable, not chemically harsh, and efficient enough that post-conjugation purification may not be required. Further this disclosure provides for reducing the logistic overheads related to product lines by eliminating the need for many unique linkers per conjugation pair.

9 Claims, 22 Drawing Sheets

Specification includes a Sequence Listing.

- Antibodies
- Nucleic acid
- Aptamers
- Proteins
- Labels
- Small molucules
- Drugs
- PHITON
- etc.

Where X and X̄ are complementary

Related U.S. Application Data

(60) Provisional application No. 62/926,037, filed on Oct. 25, 2019.

(58) Field of Classification Search
CPC ........ C12Q 2563/107; C12Q 2563/131; C12Q 2563/179
See application file for complete search history.

(56) References Cited

U.S. PATENT DOCUMENTS

| | | | |
|---|---|---|---|
| 8,445,413 | B2 | 5/2013 | Nemoto et al. |
| 8,889,350 | B2 | 11/2014 | Makarov |
| 8,946,289 | B2 | 2/2015 | Hong et al. |
| 8,946,389 | B2 | 2/2015 | Gao et al. |
| 9,612,236 | B2 | 4/2017 | Sabatte et al. |
| 2007/0238125 | A1 | 10/2007 | Uematsu et al. |
| 2015/0004598 | A1 | 1/2015 | Gao et al. |
| 2015/0344937 | A1 | 12/2015 | Flor et al. |

FOREIGN PATENT DOCUMENTS

| | | | | |
|---|---|---|---|---|
| JP | 2019528052 | A | 10/2019 | |
| WO | WO 2007/008550 | | 1/2007 | |
| WO | WO 2013/177046 | | 11/2013 | |
| WO | WO-2013188756 | A1 * | 12/2013 | .......... C12Q 1/6804 |
| WO | WO 2016/100401 | | 6/2016 | |
| WO | WO 2018/022809 | | 2/2018 | |
| WO | WO 2018/231805 | | 12/2018 | |
| WO | WO 2018/234473 | | 12/2018 | |

OTHER PUBLICATIONS

International Search Report from International Application No. PCT/US2020/057247 dated Feb. 24, 2021 (3 pages).

Written Opinion from International Application No. PCT/US2020/057247 dated Feb. 24, 2021 (7 pages).

Zhang et al., "Antibody-Linked Spherical Nucleic Acids for Cellular Targeting," *Journal of the American Chemical Society* 134:16488-16491, 2012.

Flor et al., "DNA-Directed Assembly of Anti-body-Fluorophore Conjugates for Quantitative Multiparametric Flow Cytometry," *ChemBioChem* 15(2):267-275, Jan. 24, 2014.

Park et al., "Hybridization-based aptamer labeling using complementary oligonucleotide platform for PET and optical imaging," *Biomaterials* 100:143-151, May 24, 2016.

Supplementary European Search Report from Application No. EP20879551.8 dated May 16, 2023 (8 pages).

Edward et al., "The Remarkable Flexibility of the Human Antibody Repertoire; Isolation of Over One Thousand Different Antibodies to a Single Protein, BLyS," *Journal of Molecular Biology* 334(1):103-118, 2003, published Nov. 14, 2003.

Lloyd et al., "Modelling the human immune response: performance of a 10" human antibody repertoire against a broad panel of therapeutically relevant antigens," *Protein Engineering, Design & Selection* 22(3):159-168, 2009, published Oct. 29, 2008.

Piche-Nicholas et al., "Changes in complementarity-determining regions significantly alter IgG binding to the neonatal Fc receptor (FcRn) and pharmacokinetics," *MABS* (10(1):81-94 2018, Published online Nov. 3, 2017.

* cited by examiner anti-antibody beads

PHITON beads

| | Sample Name | Subset Name |
|---|---|---|
| | 4 NB610 polyT CD3.fcs | Single Cells |
| | 3 NB610 APAB CD3.fcs | Single Cells |
| | 2 UN - Zombie.fcs | Single Cells |

| | Sample Name | Subset Name |
|---|---|---|
| | 6 NY620 polyT CD4.fcs | Single Cells |
| | 5 NY620 APAB CD4.fcs | Single Cells |
| | 2 UN - Zombie.fcs | Single Cells |

| | Sample Name | Subset Name |
|---|---|---|
| | 8 NY+NB polyT.fcs | Single Cells |
| | 7 NY+NB APAB.fcs | Single Cells |
| | 2 UN - Zombie.fcs | Single Cells |

Fluorophore

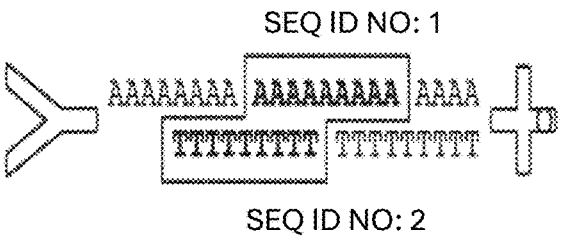
FIG. 17A
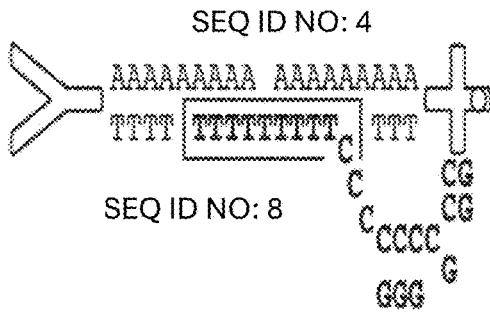
FIG. 17D
FIG. 17B
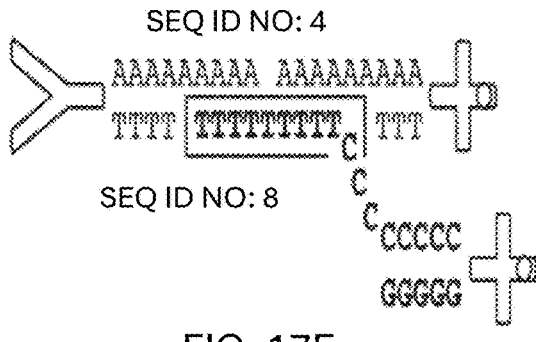
FIG. 17E
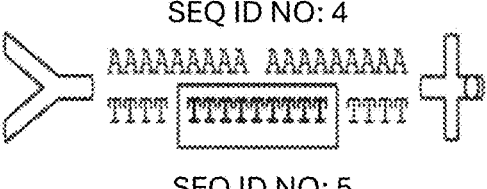
FIG. 17C
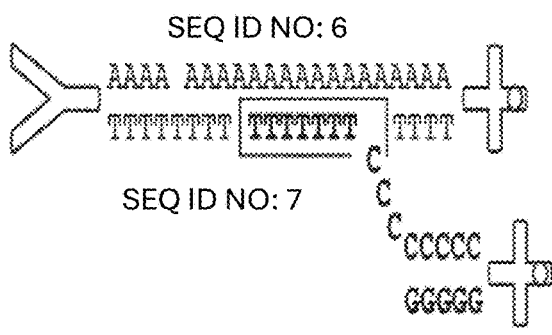
FIG. 17F

| | CD4+MFI | CD4-MFI | CD4-84th | SI |
|---|---|---|---|---|
| CD4 16/16 | 21297 | 8.66 | 91 | 257.25 |
| CD4 32/32 | 14782 | 17.3 | 103 | 171.42 |
| CD4 69/32 | 12927 | 18.8 | 99.7 | 158.76 |
| CD4 69/63 | 16921 | 14.4 | 104 | 187.75 |
| CD4 100/32 | 10049 | 27.4 | 126 | 101.13 |
| CD4 100/63 | 15919 | 30.3 | 164 | 118.24 |

POLYNUCLEOTIDE-LINKED BIOCONJUGATES AND METHODS OF MAKING AND USING

CROSS-REFERENCE TO RELATED APPLICATIONS

This application is a continuation-in-part of International Application No. PCT/US2020/057247, filed Oct. 24, 2020, which claims the benefit under 35 U.S.C. § 119 (e) of U.S. Provisional Application No. 62/926,037, filed Oct. 25, 2019. The entire contents of the aforementioned applications are incorporated by reference herein.

SEQUENCE LISTING INCORPORATION BY REFERENCE

The nucleic and amino acid sequences are shown using standard letter abbreviations for nucleotide bases, and three letter code for amino acids, as defined in 37 C.F.R. 1.822. The Sequence Listing is submitted as an ASCII text file in the form of the file named "Sequence.txt" (1,798 bytes), which was created on Sep. 17, 2025, which is incorporated by reference herein.

BACKGROUND

Current chemistries used to conjugate molecules to proteins such as antibodies are chemically harsh and involve inherent risks in altering the biological activity of the antibody and/or the molecule being conjugated to the antibody. Further, with fluorescent dye conjugated antibodies, the chemistries used produce a distribution of fluorescent dye molecules on each antibody. For example, using NHS-ester conjugation chemistry and a state-of-the-art polymer dye results in a distribution of 2-10 dye molecules that end up conjugated to each antibody in a Poisson distribution. This increases the underlying variability in measurements (and therefore noise) and also cripples the ability to quantitate biological molecules using such dye-conjugated antibodies. These conjugation chemistries are also inefficient, requiring excess dye which impacts both costs as well as raising the risk of inclusion of free, unbound dye in end products. Table 1 shows several current techniques used to attach molecules to antibodies.

TABLE 1

| Method | Description | Distinguishing features |
|---|---|---|
| NHS-ester-amine | Attachment via free primary or secondary amine groups on the surface of the antibody and an NHS-ester on the other biomolecule. | Random distribution of biomolecules over the antibody surface leads to a Poisson distribution across the population of labeled antibodies. |
| Carboxy-amine | Similar to NHS-ester attachment this method relies on a condensation reaction between a carboxylic group on either the biomolecule or antibody and a primary or secondary amine on the other. | This method suffers from a similar problem with distribution of biomolecules over the antibody as an NHS-ester method. It can also suffer from having off-target reactivity (e.g., toward phosphate groups). |
| "Click" | This method relies on functionalization of the antibody with an azide or alkyne group, depending on the specific catalyst and specific process. | Can be a chemically harsh process that limits use to "robust" antibodies. Since this method relies on another amine/carboxy conjugation method this |

TABLE 1-continued

| Method | Description | Distinguishing features |
|---|---|---|
| | | can also suffer from a wide distribution of biomolecules/antibody |
| Sulfhydryl-maleimide | This method uses free sulfhydryl groups on the surface of an antibody (or protein) to react with a maleimide group typically synthetically attached to a biomolecule of interest. | The distribution of sulfhydryl groups over the surface of an antibody are well understood but this chemistry can lead to degraded performance of the antibody and requires post-conjugation purification. |

Further, due do the potential harsh chemistries involved and the inherent "stickiness" of currently available dyes, purification of dyes following conjugation is a necessary step in current manufacturing of biomolecule conjugates.

SUMMARY

Provided for herein is a polynucleotide-modified binding molecule bioconjugate comprising a binding molecule linked to a conjugate component via a nucleic acid linker.

Provided for herein is also a polynucleotide-modified bead bioconjugate comprising a bead linked to a conjugate component via a nucleic acid linker.

Provided for herein are methods of producing a polynucleotide-modified binding molecule bioconjugate of this disclosure or a polynucleotide-modified bead bioconjugate of this disclosure comprising: (i) contacting a polynucleotide-modified substrate comprising an at least partially single-stranded nucleic acid linker with a polynucleotide-modified conjugate component comprising an at least partially single-stranded nucleic acid linker, wherein the substrate is a binding molecule or a bead, wherein at least a portion of the single-stranded linker sequence of the substrate is complementary to a portion of the single-stranded linker sequence of the conjugate component and wherein when contacted, the nucleic acid linker of the substrate and the nucleic acid linker of the conjugate component anneal to form an at least partially double-stranded linker linking the substrate to the conjugate component; (ii) contacting a substrate with a conjugate component, wherein the substrate is a binding molecule or a bead, and attaching a nucleic acid linker to the substrate and attaching the same nucleic acid linker to the conjugate component to form the polynucleotide-modified binding molecule bioconjugate, (iii) contacting a polynucleotide-modified conjugate component comprising a nucleic acid linker with a substrate, wherein the substrate is a binding molecule or a bead, and attaching the nucleic acid linker of the polynucleotide-modified conjugate component to the substrate to form the polynucleotide-modified binding molecule or bead bioconjugate, (iv) contacting a polynucleotide-modified substrate comprising a nucleic acid linker with a conjugate component, wherein the substrate is a binding molecule or a bead, and attaching the nucleic acid linker of the polynucleotide-modified substrate to the conjugate component to form the polynucleotide-modified binding molecule or bead bioconjugate; or (v) contacting (i) a polynucleotide-modified substrate comprising an at least partially single-stranded nucleic acid linker, wherein the substrate is a binding molecule or a bead, (ii) a polynucleotide-modified conjugate component comprising an at least partially single-stranded nucleic acid linker, and (iii) a further nucleic acid linker segment that is not the nucleic acid linker of (i) or (ii), wherein at least a portion of the single-stranded linker sequence of the substrate is complementary to a single-stranded portion of the further nucleic acid linker segment (iii) and/or wherein at least a portion of the single-stranded linker sequence of the conjugate component is complementary to a single-stranded portion of the further nucleic acid linker segment (iii), and wherein when contacted, the nucleic acid linker of the substrate, the nucleic acid linker of the conjugate component, and the further nucleic acid linker segment anneal to form an at least partially double-stranded linker linking the substrate to the conjugate component.

Provided for herein is a high-rate method of producing a labeled binding molecule for detection, wherein separate binding-molecule molecules of the same binding molecule are labeled with different conjugate components, the method comprising: (a) attaching an at least partially single-stranded nucleic acid linker to at least two separate binding-molecule molecules of the same binding molecule to produce a plurality of polynucleotide-modified binding-molecule molecules; and (b) contacting at least one polynucleotide-modified binding-molecule molecule of the plurality with a first polynucleotide-modified conjugate component comprising an at least partially single-stranded nucleic acid linker and contacting at least one different polynucleotide-modified binding-molecule molecule of the plurality with a second polynucleotide-modified conjugate component comprising an at least partially single-stranded nucleic acid linker, wherein the first and second polynucleotide-modified conjugate components comprise detection labels and differ at least in their detection labels, wherein at least a portion of the single-stranded sequence of the nucleic acid linker of the binding-molecule molecules is complementary to a single-stranded sequence of the nucleic acid linker of the first and/or second conjugate components, and wherein when contacted, the nucleic acid linkers anneal to form a double-stranded linker linking the binding-molecule molecules to the conjugate components.

Provided for herein is a high-rate method of producing labeled binding molecules for detection, wherein different binding molecules are labeled with the same conjugate component, the method comprising: (a) attaching an at least partially single-stranded nucleic acid linker to at least two different binding molecules to produce at least two different polynucleotide-modified binding molecules; and (b) contacting the at least two different polynucleotide-modified binding molecules with a polynucleotide-modified conjugate component comprising a detection label and comprising an at least partially single-stranded nucleic acid linker, wherein at least a portion of the single-stranded sequence of the nucleic acid linker of the binding molecules is complementary to a single-stranded sequence of the nucleic acid linker of the conjugate component and wherein when contacted the nucleic acid linkers anneal to form a double-stranded linker linking the binding molecules to the conjugate component.

Provided for herein is a composition comprising: (i) (a) a substrate comprising an at least partially single-stranded nucleic acid linker, wherein the substrate is a binding molecule or a bead, and (i) (b) a conjugate component comprising an at least partially single-stranded nucleic acid linker, wherein at least a sufficient portion of the single-stranded sequence of the nucleic acid linker of the substrate is complementary to a portion of the single-stranded sequence of the nucleic acid linker of the conjugate component to allow for the linkers to anneal and form an at least partially double-stranded linker linking the substrate to the conjugate component; (ii) (a) a substrate comprising a nucleic acid linker, wherein the substrate is a binding molecule or a bead, and (ii) (b) a conjugate component capable of attachment to the nucleic acid linker to link the substrate to the conjugate component; (iii) (a) a conjugate component comprising a nucleic acid linker, (iii) (b) a substrate capable of attachment to the nucleic acid linker to link the conjugate component to the substrate; (iv) (a) a substrate capable of attachment to a nucleic acid linker, wherein the substrate is a binding molecule or a bead, and a conjugate component capable of attachment to a nucleic acid linker, and (iv) (b) a nucleic acid linker, wherein the nucleic acid linker is single-stranded, comprises a double-stranded segment, or wherein the nucleic acid linker is entirely double stranded; or (v)(a) a substrate comprising an at least partially single-stranded nucleic acid linker, wherein the substrate is a binding molecule or a bead, (v)(b) a conjugate component comprising an at least partially single-stranded nucleic acid linker; and (v)(c) a further nucleic acid linker segment, wherein (v)(a), (v)(b), and (v)(c) can anneal to form an at least partially double-stranded nucleic acid linker comprising (v)(a), (v)(b), and (v)(c) and linking (v)(a) to (v)(b).

Provided for herein is a method of labeling a cell, tissue, and/or organ, the method comprising contacting the cell, tissue, and/or organ with a polynucleotide-modified binding molecule bioconjugate of this disclosure wherein the binding molecule portion of the bioconjugate binds to an antigen, epitope, and/or hapten of the cell, tissue, and/or organ and wherein the conjugate component portion of the bioconjugate comprises a detectable label.

Provided for herein is a method of quantitatively measuring a signal from a labeled cell, tissue, and/or organ, the method comprising contacting the cell, tissue, and/or organ with a polynucleotide-modified binding molecule bioconjugate of this disclosure wherein the binding molecule portion of the bioconjugate binds to an antigen, epitope, and/or hapten of the cell, tissue, and/or organ and the conjugate component portion of the bioconjugate comprises a detectable label and measuring the presence of the polynucleotide-modified binding molecule bioconjugate wherein the DoL of the binding molecule is known, thus allowing a quantitative measurement to be made.

Provided for herein is a method of tuning the brightness of a polynucleotide-modified biomolecule bioconjugate of the present disclosure, the method comprising i) altering the total length of the nucleic acid linker, ii) altering the length of the fully double-stranded region of the nucleic acid linker, iii) altering the length of the single-stranded portion of the nucleic acid linker, and/or iv) having the single-stranded portion comprise a polyA, polyT, polyG, polyC sequence and/or a unique nucleic acid sequence.

Provided for herein is a kit comprising one or more components necessary to produce the polynucleotide-modified binding molecule bioconjugate of this disclosure, to produce the polynucleotide-modified bead bioconjugate of this disclosure, to produce a composition of this disclosure, or to perform any of the methods of this disclosure.

BRIEF DESCRIPTION OF THE DRAWINGS

FIGS. 17A through 17F show several illustrative examples of the inclusion of an additional nucleic acid molecule (boxed) in the linker linking the substrate to the conjugate component, wherein the additional nucleic acid molecule is in addition to a linker (SEQ ID NOs: 1-8) attached to the substrate and in addition to a linker attached to the conjugate component.

DETAILED DESCRIPTION

Definitions

Figure 1:
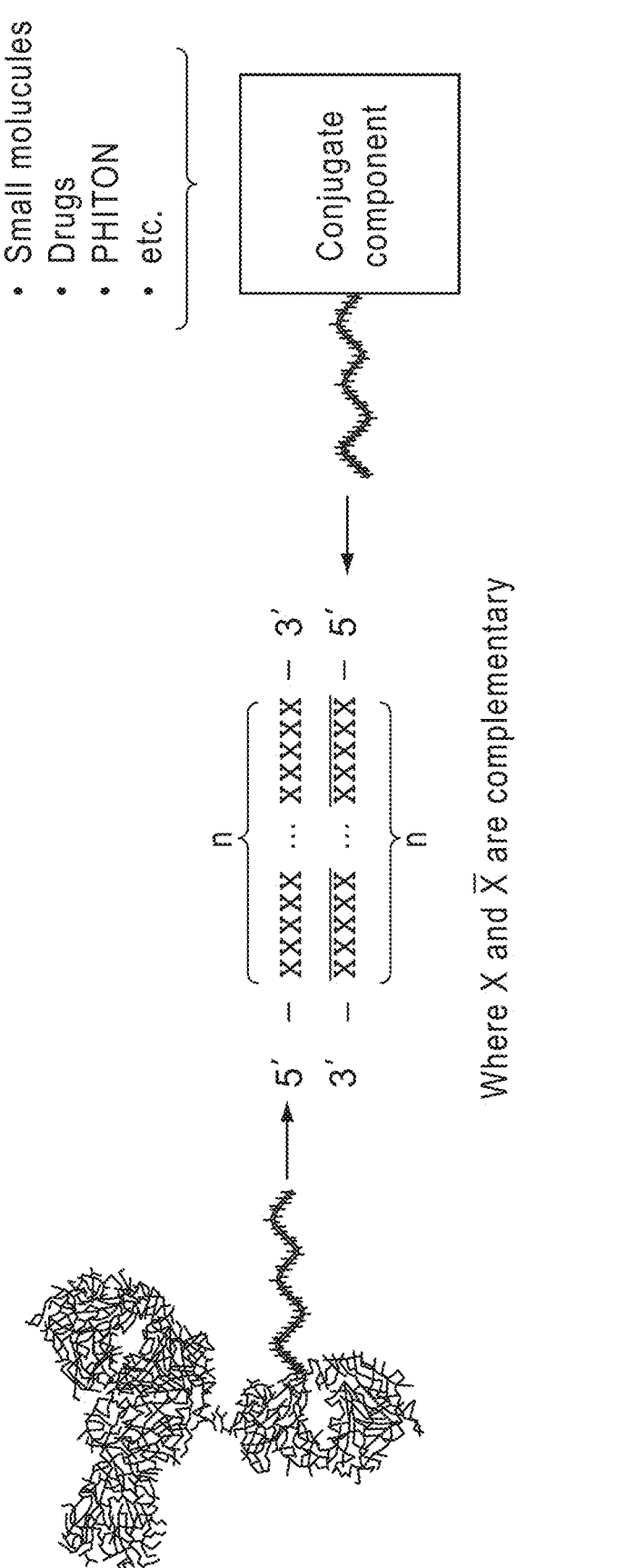
FIG. 1 shows an illustrative example of the component parts of a polynucleotide-modified antibody bioconjugate of this disclosure (a polynucleotide-modified antibody, a double-stranded polynucleotide linker with complementary nucleic acid strands, and a polynucleotide-modified conjugate component).
Figure 2:
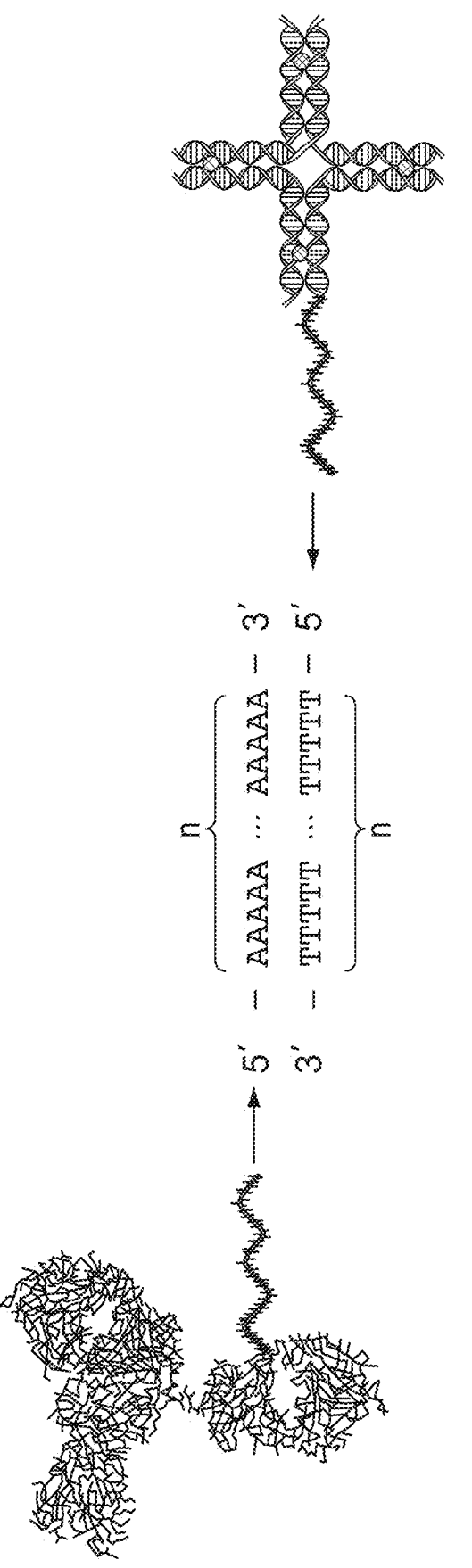
FIG. 2 shows another illustrative example of the component parts of a polynucleotide-modified antibody bioconjugate of this disclosure (a polynucleotide-modified antibody, a double-stranded polynucleotide linker with complementary polyA and polyT nucleic acid strands, and an oligonucleotide-based fluorescent label).

It is to be noted that the term "a" or "an" entity refers to one or more of that entity; for example, "a linker," is understood to represent one or more linkers. As such, the terms "a" (or "an"), "one or more," and "at least one" can be used interchangeably herein.

Furthermore, "and/or" where used herein is to be taken as specific disclosure of each of the specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising" or "comprises" otherwise analogous aspects described in terms of "consisting of," "consists of," "consisting essentially of," and/or "consists essentially of," and the like are also provided.

Unless defined otherwise, technical and scientific terms used herein have the same meaning as commonly understood by one of ordinary skill in the art to which this disclosure is related.

Numeric ranges are inclusive of the numbers defining the range. Even when not explicitly identified by "and any range in between," or the like, where a list of values is recited, e.g., 1, 2, 3, or 4, unless otherwise stated, the disclosure specifically includes any range in between the values, inclusive of the end-points, e.g., 1 to 3, 1 to 4, 2 to 3, 2 to 4, etc.

The headings provided herein are solely for ease of reference and are not limitations of the various aspects or aspects of the disclosure, which can be had by reference to the specification as a whole.

As used herein, a "linker" is a constituent of a conjugated molecule whose purpose is to link together other constituents of the molecule or, when the other constituents of the conjugated molecule are not linked together, the portion of a constituent present for the purpose of conjugating to another constituent but that would otherwise not necessarily be present. For example, an antibody would not normally or necessarily have a polynucleotide attached to it, but for the purposes of this disclosure, a polynucleotide can be attached to an antibody to form a linker to link the antibody to another molecule to form a polynucleotide-modified antibody bioconjugate.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/ blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein, but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Derivatives are polypeptides that have been altered so as to exhibit additional features not found on the native polypeptide. Examples include fusion proteins. Derivative polypeptides can also be referred to herein as "polypeptide analogs." As used herein a "derivative" can refer to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

As used herein, the term "binding molecule" refers in its broadest sense to a molecule that specifically binds to another target molecule, moiety, or antigen. Binding molecules include those that can specifically bind to an antigenic determinant, such as an antibody, and also molecules that can bind to receptors, such as receptor ligands (e.g., gastrin-releasing peptide (GRP) and gastrin-releasing peptide receptor (GRPR)). Thus, representative examples of binding molecules include peptides, recombinant, natural, or engineered receptor/ligand proteins, aptamers, tetramers (folded MHC proteins with peptides used for detecting T cell receptors), non-antibody proteins or antibody mimetics, e.g., affilins, affimers, affitins, alphabodies, avimers, fynomers, Kunitz domain peptides, nanoCLAMPS, Designed Ankyrin Repeat Proteins (DARPins), monobodies, nanobodies, anticalins, affibodies, and SOMAmers (further examples are referred to in the Global Bioanalysis Consortium (GBC) and the European Medicines Agency "classification of critical reagents as analyte specific or binding reagents, specifically antibodies; peptides; engineered proteins; antibody, protein and peptide conjugates; reagent drugs; aptamers and anti-drug antibody (ADA) reagents including positive and negative controls (King et al. 2014)).

Disclosed herein are certain binding molecules comprising antibodies, or antigen-binding fragments, variants, or derivatives thereof. Unless specifically referring to full-sized antibodies such as naturally-occurring antibodies, the term "binding molecule" encompasses full-sized antibodies including bispecific antibodies (e.g., comprising a first binding domain binding to a first epitope, and a second binding domain binding to a second epitope), as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

The terms "antibody" and "immunoglobulin" can be used interchangeably herein. Basic immunoglobulin structures in vertebrate systems are relatively well understood. See, e.g., Harlow et al., Antibodies: A Laboratory Manual, (Cold Spring Harbor Laboratory Press, 2nd ed. 1988). Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The term "bispecific antibody" as used herein refers to an antibody that has binding sites for two different antigens within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, Future Oncol. 6:1387-94 (2010); Mabry and Snavely, IDrugs. 13:543-9 (2010)). A bispecific antibody can also be a diabody.

As used herein, the term "engineered antibody" refers to an antibody in which the variable domain in either the heavy and light chain or both is altered by at least partial replacement of one or more CDRs from an antibody of known specificity and, by partial framework region replacement and sequence changing. Although the CDRs can be derived from an antibody of the same class or even subclass as the antibody from which the framework regions are derived, it is envisaged that the CDRs will be derived from an antibody of different class, e.g., from an antibody from a different species. An engineered antibody in which one or more "donor" CDRs from a non-human antibody of known specificity is grafted into a human heavy or light chain framework region is referred to herein as a "humanized antibody." In some instances, not all of the CDRs are replaced with the complete CDRs from the donor variable region to transfer the antigen binding capacity of one variable domain to another; instead, minimal amino acids that maintain the activity of the target-binding site are transferred. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

The term "polynucleotide" is intended to encompass a singular nucleic acid as well as plural nucleic acids with "nucleic acid" referring to, for example, DNA or RNA or an analog thereof such as comprising a synthetic base. In certain embodiments, the polynucleotide or nucleic acid is DNA. In other embodiments, a polynucleotide can be RNA. A nucleic acid or polynucleotide can comprise a conventional phosphodiester bond or a non-conventional bond (e.g., an amide bond, such as found in peptide nucleic acids (PNA)). By "isolated" nucleic acid or polynucleotide is intended a nucleic acid molecule, e.g., DNA or RNA, which has been removed from its native environment such as an isolated nucleic acid molecule or construct, e.g., messenger RNA (mRNA) or plasmid DNA (pDNA). For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein the terms "treat," "treatment," or "treatment of" (e.g., in the phrase "treating a subject") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, camelids, bears, and so on. Mammalian subjects also include animals in the wild such as elephants, giraffes, deer, kangaroos, large cats, etc.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of a reagent as disclosed herein is an amount sufficient to carry out a specifically stated purpose. An "effective amount" can be determined empirically and in a routine manner, in relation to the stated purpose.

As used herein, the term "bioconjugate" invokes the use of a biological linker (i.e., a nucleic acid linker) and refers to a substrate molecule (for example a binding molecule or a bead as described elsewhere herein) linked via a nucleic acid linker to a conjugate component (as disclosed anywhere herein), regardless of the biological or synthetic origin of the substrate molecule and/or the conjugate component.

As used herein, the term "bead" refers to a "polystyrene microsphere" and the terms are used interchangeable throughout. In certain embodiments, labels (e.g., PHITONS) can be internalized into a bead by forming a polymer microsphere with dopant.

As used herein, a "PHITON" is an oligonucleotide-based nanoparticle produced by Phitonex, Inc. (now a part of Thermo Fisher Scientific), Durham, North Carolina. Examples of PHITON polynucleotide-modified conjugate components are NOVAFLUOR polynucleotide-modified conjugate components (Thermo Fisher Scientific, Waltham, MA). As used herein, the term "NovaBlue" is interchangeable with the term "NOVAFLUOR Blue". As used herein, the term "NovaYellow" is interchangeable with the term "NOVAFLUOR Yellow".

As used herein, unless otherwise specified, "complementary base pairing" refers to A/T, A/U, or C/G base pairing and corresponding pairing of synthetic or non-standard nucleotides, e.g., isocytosine/isoguanine (isoC/isoG). To the extent that thymidine (T) is specified as a base in a nucleic acid, for the purposes of simplifying this disclosure, unless otherwise specified, it is understood that uracil (U) is intended if the nucleic acid is RNA.

Unless otherwise specified in a particular context, the terms "conjugated to" and "linked to" are used interchangeably herein.

As used herein, the acronym "SKU" refers to a "stock keeping unit."

As used herein, an "at least partially single-stranded" nucleic acid and the like can be entirely single-stranded or can comprise both single- and double-stranded portions but is not entirely double-stranded. A nucleic acid that is "at least partially double-stranded," "comprises a double-stranded segment," and the like, can be entirely double-stranded or can comprise both single- and double-stranded portions but is not entirely single-stranded. One of ordinary skill in the art will recognize that when a nucleic acid linker of an element (such as a substrate or conjugate component) is intended to hybridize with a nucleic acid linker of another element, the single-stranded portion or each linker is sufficient in length and continuity to allow for hybridization.

Overview

Provided herein is a method for creating a bioconjugate as described anywhere herein that is stable, not chemically harsh, and efficient enough to preclude purification in certain embodiments. In certain embodiments, the method does not involve any biologically incompatible reagents, pH changes outside of physiological conditions, high temperatures, or high salt concentrations. Further (as shown in Example 2 below), in certain embodiments, there is no exchange of the species in solution due to the high thermodynamic stability of the linker. The method is also rapid and scalable for manufacturing, and can be used to pair and link together various molecules to one another.

One important aspect of this disclosure involves reducing the logistic overheads related to product lines by eliminating the need for many unique linkers per conjugate-antibody pair. This can have a dramatic effect on the scale of manufacturing (e.g. by only having 1 SKU per dye with the polynucleotide) and rapidly conjugate these dyes to antibodies (1 SKU per antibody with the complementary polynucleotide). For example, when creating a library of PHITON-antibody bioconjugates, every PHITON can be modified with the same polynucleotide and every antibody can be modified with the same complementary polynucleotide, rather than require a unique set of complementary polynucleotides for each PHITON-antibody bioconjugate.

Also provided herein are kits for conjugating, for example, an oligonucleotide-based fluorescent label (e.g., PHITON) to antibodies (or other molecules).

Certain embodiments are drawn to a polynucleotide-modified substrate bioconjugate (also referred to as polynucleotide-modified bioconjugate) comprising a substrate linked to a conjugate component via a nucleic acid linker, wherein the nucleic acid linker is described in detail below. In certain embodiments, the substrate is a binding molecule. In certain embodiments, the substrate is a bead (aka, polystyrene microsphere).

By "polynucleotide-modified binding molecule," it is meant a binding molecule to which a nucleic acid/polynucleotide is attached. Although not limiting, one of ordinary skill in the art will be familiar with a number of conjugation chemistries such as NHS-esters, maleimides, and "click," that can be used to attach nucleic acids to other molecules such as proteins/antibodies, i.e., to make a polynucleotide-modified binding molecule of this disclosure. Thus, a "polynucleotide-modified binding molecule bioconjugate" is a polynucleotide-modified binding molecule linked to a conjugate component.

By "polynucleotide-modified bead," it is meant a bead to which a nucleic acid/polynucleotide is attached. Although not limiting, one of ordinary skill in the art will be familiar with functionalizing the surface of a bead to add a polynucleotide, for example, using the same chemistries described for antibody-polynucleotide conjugation. Thus, a "polynucleotide-modified bead bioconjugate" is a polynucleotide-modified bead linked to a conjugate component. In certain embodiments, the nucleic acid is single-stranded and attached to the bead at its 5'-end. In certain embodiments, the nucleic acid is single-stranded and attached to the bead at its 3'-end.

One of ordinary skill in the art would understand that nucleic acid molecules can be single-stranded, double-stranded, or comprise both single-stranded and double-stranded segments. Further, nucleic acid molecules can also comprise triple-stranded and less organized forms. In certain embodiments, the nucleic acid linker comprises or consists of a single-stranded segment. In certain embodiments, the nucleic acid linker comprises or consists of a double-stranded segment. In certain embodiments, the nucleic acid linker has both single-stranded and double-stranded segments. In certain embodiments, the linker does not contain a nucleic acid sequence known to those of ordinary skill in the art for use in RNA destruction, RNA sequencing, or "barcoding" (a "barcode" sequence is a unique polynucleotide sequence for uses known to those in the art, for example, for species identification using a short section of DNA from a specific gene or genes).

While complementary bases/segments of a nucleic acid linker strand from the substrate and a nucleic acid linker strand from the conjugate component can anneal to link the substrate to the conjugate component, it is understood that in certain embodiments, the nucleic acid linker strand of the substrate is not attached and/or covalently bonded to the conjugate component. In certain embodiments, the nucleic acid linker strand of the conjugate component is not attached and/or covalently bonded to the substrate. In certain embodiments, the nucleic acid linker strand of the substrate is not attached and/or covalently bonded to the conjugate component and the nucleic acid linker strand of the conjugate component is not attached and/or covalently bonded to the substrate. Thus, in certain embodiments, the substrate and the conjugate component are not covalently bonded to each other through any linkage and are instead held together by the annealed portion of the nucleic acid linker. In certain embodiments, a nucleic acid is attached to a substrate at its 5'-end. In certain embodiments, a nucleic acid is attached to a conjugate component at its 5'-end or is an extension of a 5'-end. In certain embodiments, a nucleic acid is attached to a substrate at its 3'-end. In certain embodiments, a nucleic acid is attached to a conjugate component at its 3'-end or is an extension of a 3'-end.

The nucleic acid linker can be of any length but certain considerations can be taken into account. For example, an extremely short linker may bring an antibody or bead and the conjugate component into too close of contact, resulting in steric hindrance or other interference. On the other hand, a very long linker may be more difficult to produce or may not keep the antibody or bead within a sufficient distance of a dye or label such that the signal of the dye or label is not accurately attributable to the attached antibody or bead. In certain embodiments, the nucleic acid linker is at least about 10, 11, 12, 13, 14, 15, 16, 17, 18, 19, 20, 25, 30, 35, 40, 45, 50, 55, 60, 65, 70, 75, 80, 85, 90, 95, 100 nucleotides in length. In certain embodiments, the nucleic acid linker is from any of about 10, 11, 12, 13, 14, 15, 16, 17, 18, 19, 20, 25, 30, 35, 40, 50, or 60 nucleotides in length to any of about 11, 12, 13, 14, 15, 16, 17, 18, 19, 20, 25, 30, 35, 40, 50, 60, or 75 nucleotides in length. In certain embodiments, the nucleic acid linker is from any of about 10, 15, 20, 25, 30, 35, 40, or 50 nucleotides in length to any of about 15, 20, 25, 30, 35, 40, 50, or 75 nucleotides in length. In certain embodiments, the nucleic acid linker is from any of about 15, 20, 25, 30, or 35 nucleotides in length to any of about 20, 25, 30, 35, or 40 nucleotides in length. In certain embodiments, the conjugate component comprises or consists of a nucleic acid. In certain embodiments, the nucleic acid linker can be an extension of a nucleic acid molecule of the conjugate component. For purposes of this disclosure, it is understood that even when the conjugate component itself comprises or is entirely made of one or more nucleic acid molecules, it is considered a "polynucleotide-modified conjugate component" when comprising a nucleic acid linker sequence. For example, where the conjugate component is an oligonucleotide-based fluorescent label, e.g. a PHITON, the length of the linker is determined from the "edge" of the conjugate component, wherein the edge is determined as the end of any single-stranded segment longer than four nucleotides. In certain embodiments where the conjugate component comprises a nucleic acid, the nucleic acid of the conjugate component has a length of at least 10, 15, 20, 25, 30, 35, 40, 50, 55, 60, 65, 75, 80, 85, 90, 95, 100, 110, 120, 130, 140, 150, 175, 200, 300, 400, 500, 750, 1000, 2000, 3000, 4000, 5000, 7500, or 10000 nucleotides, or any range in between, not including the nucleic acid linker. In certain embodiments where the conjugate component comprises a nucleic acid, the nucleic acid of the conjugate component has a length of at least 10, 15, 20, 25, 30, 35, 40, 50, 55, 60, 65, 75, 80, 85, 90, 95, 100, 110, 120, 130, 140, 150, 175, 200, 300, or 400 nucleotides, or any range in between, not including the nucleic acid linker. In certain embodiments where the conjugate component comprises a nucleic acid, the nucleic acid of the conjugate component has a length of at least 20, 25, 30, 35, 40, 50, 55, 60, 65, 75, 80, 85, 90, 95, 100, 110, or 120 nucleotides, or any range in between, not including the nucleic acid linker. In certain embodiments where the conjugate component comprises a nucleic acid, the nucleic acid of the conjugate component has a tertiary and/or a quaternary structure. As noted, the nucleic acid linker can include both single-stranded and double-stranded segments. In certain embodiments, the double-stranded segment of the nucleic acid linker is at least about 10, 15, 20, 25, 30, 35, 40, 50, 60, 65, 70, 75, 80, 85, 90, 95 or 100 nucleotides in length. In certain embodiments, the double-stranded segment of the nucleic acid linker is any of about 10, 15, 20, 25, 30, 35, 40, 45, 50, 55, 60, 65, 70 or 75 nucleotides in length to any of about 15, 20, 25, 30, 35, 40, 45, 50, 55, 60, 65, 70, 75, 80, 85, 90, 95 or 100 nucleotides in length. One of ordinary skill in the art will recognize that whereas double-stranded nucleic acids are generally thought to be made of annealed sequences of complementary base pairs, not all the pairing in a double-stranded nucleic acid segment need be complementary. There is some tolerance for two strands of nucleic acids comprising complementary bases to anneal to form a double-stranded nucleic acid incorporating some non-complementary base paring. Also, degenerate (universal) bases such as deoxyinosine exist that can pair with numerous bases. In certain embodiments, the double-stranded segment of the nucleic acid linker comprises at least about 10, 15, 20, 25, 30, 35, 40, 45, 50, 55, 60, 65, 70, or 75 complementary base pairs, even if the double-stranded segment is not entirely composed of complementary base pairs. In certain embodiments, the double-stranded segment of the nucleic acid linker comprises from any of about 10, 15, 20, 25, 30, 35, 40, 50, or 60 complementary base pairs to any of about 15, 20, 25, 30, 35, 40, 50, 60, or 75 complementary base pairs, even if the double-stranded segment is not entirely composed of complementary base pairs. In certain embodiments, at least 85%, 90%, 95%, or 98% of the double-stranded segment of the nucleic acid linker is complementary base paired. In certain embodiments, the double-stranded segment of the nucleic acid linker has no more than 1, 2, 3, 4, 5, 6, 7, 8, 9, 10, or 11 mismatched base pairs. In certain embodiments, however, 100% of the double-stranded segment is complementary base paired. In certain embodiments, the double-stranded segment comprises at least about 7, 8, 9, 10, 11, 12, 13, 14, 15, 16, 17, 18, 19, 20, 25, 30, 40, 50, 60, or 75 consecutive complementary base pairs or from any of about 7, 8, 9, 10, 15, 20, 25, 30, 35, 40, 50, or 60 consecutive complementary base pairs to any of about 8, 9, 10, 15, 20, 25, 30, 35, 40, 50, 60, or 75 consecutive complementary base pairs.

The effect of the nucleic acid linker composition and length of the double-stranded portion was investigated in Example 5 and is shown in FIG. 19A through FIG. 21B. A variety of antibody-fluorescent polynucleotide-modified conjugate component conjugates were made and are depicted in FIG. 19B. Some of the conjugates had a short, fully double-stranded linker as seen in FIG. 19B, conjugates 16/16 and 32/32, whereas others had a longer nucleic acid linker that was partially double-stranded as seen in FIG. 19B, conjugates 69/32, 69/63, 100/32 and 100/63. As shown in FIGS. 20A-20D, the composition of the linker strongly influenced the performance of the conjugates in flow cytometry, as measured by the median fluorescence intensity (MFI) of the conjugates. Surprisingly, it was found that the shorter linkers that were fully double-stranded had the best performance, see FIGS. 20A-20D, conjugates 16/16 and 69/63. Intermediate performance was seen with the 32-mer or the partially double-stranded linker with an exposed poly(T) region, see FIGS. 20A-20D, conjugates 32/32 and 100/63. The poorest performance was observed with partially double-stranded linkers with an exposed unique identifying sequence, see FIGS. 20A-20D, conjugates 69/32 and 100/32. Thus, the nucleic acid linker composition and length of the double-stranded portion of the nucleic acid linker can be used to tune the brightness of the polynucleotide-modified antibody bioconjugates and polynucleotide-modified biomolecule bioconjugates provided herein.

Accordingly, provided herein is a method of tuning the brightness of a polynucleotide-modified biomolecule bioconjugate of the present disclosure, the method comprising i) altering the total length of the nucleic acid linker, ii) altering the length of the fully double-stranded region of the nucleic acid linker, iii) altering the length of the single-stranded portion of the nucleic acid linker, and/or iv) having the single-stranded portion comprise a polyA, polyT, polyG, polyC sequence and/or a unique nucleic acid sequence. In certain embodiments, a method of increasing the brightness of a polynucleotide-modified biomolecule bioconjugate of the present disclosure is provided, the method comprising, i) decreasing the total length of the nucleic acid linker to 70 nucleotides or fewer, and/or ii) increasing the length of the fully double-stranded region of the nucleic acid linker. In certain embodiments, the nucleic acid linker is fully double-stranded. In certain embodiments, the nucleic acid linker is mostly double-stranded. In certain embodiments, the nucleic acid linker is 70 nucleotides or fewer, 60 nucleotides or fewer, 50 nucleotides or fewer, 40 nucleotides or fewer, 30 nucleotides or fewer, or 20 nucleotides or fewer. In certain embodiments, the nucleic acid linker is between 10 and 70 nucleotides in length, between 10 and 60 nucleotides in length, between 10 and 50 nucleotides in length, between 10 and 40 nucleotides in length, between 10 and 30 nucleotides in length, or between 10 and 20 nucleotides in length.

While not limited to any particular complementary sequences, in certain embodiments, the nucleic acid linker can comprise complementary polyadenosine (polyA) and polythymidine (polyT) sequences and/or complementary polycytosine (polyC) and polyguanidine (polyG) sequences. For example, the C: G content of a nucleic acid is known to be a key thermodynamic determinate of double-stranded interactions. In certain embodiments, the double-stranded segment of the nucleic acid linker comprises a polyA sequence in one strand and a polythymidine polyT sequence in the other strand. In certain embodiments, the double-stranded segment of the nucleic acid linker comprises a polyC sequence in one strand and a polyG sequence in the other strand. In certain embodiments, the double-stranded segment of the nucleic acid linker comprises polyA and polyC sequences in one strand and polyT and polyG sequences in the other strand. In certain embodiments, the double-stranded segment of the nucleic acid linker comprises polyA and polyG sequences in one strand and polyT and polyC sequences in the other strand. In certain embodiments, the double-stranded segment of the nucleic acid linker comprises polyA, polyT, polyC, and/or polyG sequences in one strand and polyT, polyA, polyG, and/or polyC sequences in the other strand. In certain embodiments, the double-stranded segment of the nucleic acid linker consists of a polyadenosine sequence (polyA) in one strand and a polythymidine sequence (polyT) in the other strand. In certain embodiments, the double-stranded segment of the nucleic acid linker consists of a polycytosine sequence (polyC) in one strand and a polyguanidine sequence (polyG) in the other strand. One of ordinary skill in the art reading this disclosure will understand that it is contemplated that any nucleic acid linker of any of the embodiments herein can have the above compositions.

While not limited to any particular complementary sequences, in certain embodiments, the nucleic acid linker comprises a unique identifying sequence. For purposes of the nucleic acid linker, a "unique identifying sequence" is an oligonucleotide sequence that can be used to distinguish between one or multiple species, for example, one to which a complementary primer sequence can bind to for downstream amplification (such as by PCR), long-read sequencing, or next generation sequencing (NGS), or alternatively, that can be probed using a complementary sequence, e.g., through fluorescent in situ hybridization (FISH). In certain embodiments, a double-stranded segment of a nucleic acid linker comprises a unique identifying sequence. In certain embodiments, the unique identifying sequence can be used for nucleic acid amplification such as by PCR. In certain embodiments, the unique identifying sequence can be used for next-generation sequencing (NGS). In certain embodiments, a nucleic acid linker comprises a sequence enabling it to be filtered out in downstream sequencing applications. For example, wherein the sequence is distinguishable from other nucleotide sequences in sequencing through the use of a unique sequence, e.g., one to which a complementary primer sequence can bind, enabling filtering of all linker-tagged species to be excluded from downstream analysis. In certain embodiments, the nucleic acid linker comprises a sequence for specific binding by a third biomolecule and/or for targeted gene editing through enzymatic cleavage (e.g., CRISPR, Zinc-finger nucleases, restriction enzymes). For example, wherein the sequence is designed to enable targeting through a CRISPR gRNA and this targeting and cleaved by CRISPR, or for example, wherein a target site for the DNA-binding domain of a Zinc-finger nuclease, or alternatively, a sequence that is specifically targeted for cleavage by a restriction enzyme, e.g., EcoRI endonuclease, which cleaves the DNA sequence GAATTC. In certain embodiments, the nucleic acid linker comprises one or more unique sequences enabling enzymatic or binding activity. In certain embodiments, a unique sequence enabling enzymatic or binding activity is present in the double-stranded segment.

In certain embodiments, the nucleic acid linker can be comprised of one or more nucleic acid molecules that are not attached to either the substrate or the conjugate component. For example, an additional nucleic acid molecule could serve as a "bridge," bringing together the nucleic acid linker attached to the substrate and the nucleic acid linker attached to or an extension of the conjugate component. In certain embodiments, the additional nucleic acid could be a second attachment point to the conjugate component or substrate. The additional nucleic acid molecule could also attach to an additional component such as an additional substrate or addition conjugate component, linking together a first substrate and a first conjugate component with a second substrate or further substrates and/or second conjugate component or further conjugate components (FIGS. 17A-17F). In certain embodiments, a nucleic acid linker comprises (i) a portion attached to the substrate, (ii) a portion attached to or an extension of the conjugate component, and (iii) at least one additional portion that is not (i) or (ii). In certain embodiments, (iii) is a second portion attached to or an extension of the conjugate component or attached to or an extension of an additional conjugate component. In certain embodiments, (iii) is a second portion attached to the substrate or attached to an additional substrate.

The term "conjugate component" as used in this disclosure, unless specified otherwise in a particular context, refers to any constituent linked to a substrate (e.g., a binding molecule or bead) via a nucleic acid linker as disclosed herein to form a bioconjugate. Representative examples of conjugate components include an antibody or an antigen-binding fragment, variant, or derivative thereof, a nucleic acid, an aptamer, a protein, a dye or label, a small molecule, a therapeutic peptide, a receptor ligand, a pharmaceutically active agent, or an oligonucleotide-based fluorescent label. In certain embodiments, for example wherein the conjugate component is an antibody which is linked to another antibody, the distinction between which antibody is the conjugate component is not limiting where the two are linked by a nucleic acid linker. In certain embodiments, the conjugate component is an oligonucleotide-based fluorescent label. For example, in certain embodiments, the conjugate component is a PHITON as defined elsewhere herein. As in certain embodiments, the conjugate component comprises or is a nucleic acid, and the linker is a nucleic acid, in certain embodiments, the linker is an extension of a nucleic acid strand of the conjugate component rather than "attached" to the conjugate component as, for example, a nucleic acid linker would be attached to an antibody or bead.

In certain embodiments, the degree-of-labeling (DoL) (also referred to in the art as dye to protein (D:P) or fluorophore to protein (F:P)) of the binding molecule or bead is controlled stoichiometrically. This can be achieved, for example, via the availability of the nucleic acid to be attached. In certain embodiments, the DoL of the binding molecule is between any of 1, 2, 3, 4, 5, 6, 7, 8, 9, or 10 and any of 2, 3, 4, 5, 6, 7, 8, 9, 10, or 11. In certain embodiments, the DoL of the binding molecule or bead is 1, 2, 3, 4, 5, 6, 7, 8, 9, 10, 11, 12, 13, 14, 15, 16, 17, 18, 19, or 20. The DoL of the nucleic acids on a polynucleotide-modified binding molecule can be independent of the DoL of the conjugate component and in certain embodiments is 1, 2, 3, 4, 5, 6, 7, 8, 9, 10, or 11, or any range in between, inclusive of the endpoints. In certain embodiment, the DoL of the bead is between any of about 100, 1,000, 10,000, or 100,000 and any of about 1,000, 10,000, 100,000, or 1,000,000. In certain embodiments, the degree-of-labeling (DoL) of the nucleic acids on a polynucleotide-modified bead is independent of the DoL of the conjugate component.

The polynucleotide-modified bioconjugate of this disclosure is contemplated for use in numerous applications. For example, in certain embodiments, the bioconjugate can be used to specifically label a cell, tissue, and/or organ for one or more of flow cytometry, antibody screening, ELISA or other sandwich assays, immune monitoring, biomarker assays, lateral flow, point-of-care/rapid diagnostics, imaging, microscopy, molecular diagnostics, next generation sequencing, long read sequencing, in situ sequencing, polymerase chain reaction, microarrays, nucleic acid sequencing, amino acid sequencing, digital pathology, Southern blotting, Northern blotting, Western blotting, as a reference sample such as a control or for calibration of an instrument, assay, or system, or prophylactic and/or therapeutic purposes.

Figure 18:
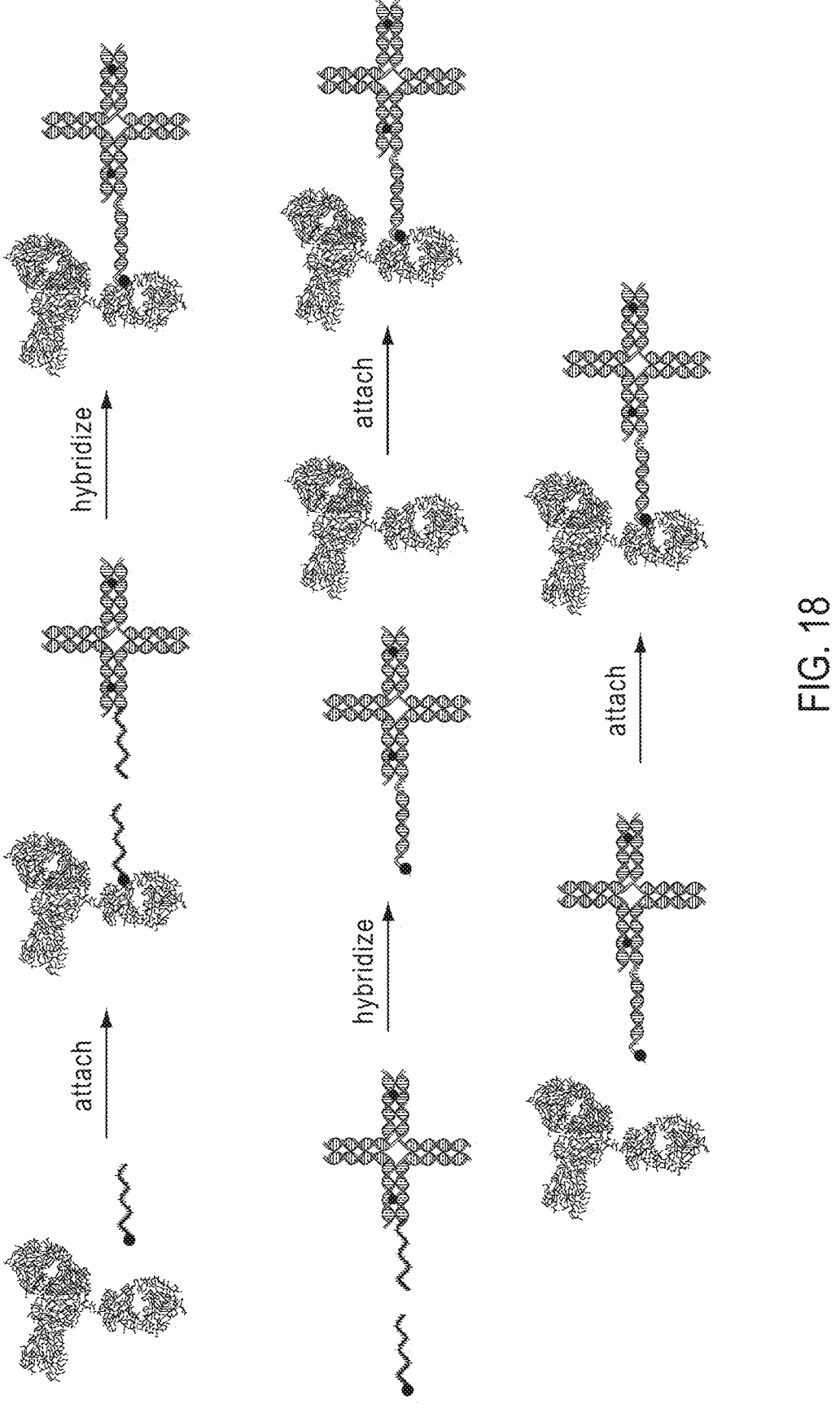
FIG. 18 shows illustrative examples of (top) linking a substrate to a conjugate component indirectly by hybridizing the respective complementary single-stranded portions of their linkers, (middle) linking a substrate to a conjugate component by first hybridizing a free linker to a complementary linker attached to or an extension of a conjugate component to form an at least partially double-stranded linker and then directly attaching at least one strand of the linker to a substrate, and (bottom) directly attaching a linker that is attached to or an extension of a conjugate component to a substrate.

Provided for herein are methods for producing polynucleotide-modified bioconjugates such as the polynucleotide-modified binding molecule bioconjugate and polynucleotide-modified bead bioconjugate of this disclosure. In certain embodiments, the method comprises contacting a polynucleotide-modified substrate comprising an at least partially or fully single-stranded nucleic acid linker with a polynucleotide-modified conjugate component with an at least partially or fully single-stranded nucleic acid linker (FIG. 18, top). In certain embodiments, the substrate is a binding molecule. In certain embodiments, the substrate is a bead. In certain embodiments, in order to form a double-stranded nucleic acid linker, at least a portion of the single-stranded linker sequence of the substrate is complementary to a portion of the single-stranded linker sequence of the conjugate component. When contacted, the nucleic acid linker of the substrate and the nucleic acid linker of the conjugate component can anneal to form an at least partially double-stranded linker linking the substrate to the conjugate component. Many possible substrates, such as binding molecules (e.g., antibodies) or beads, may require that a nucleic acid linker be chemically attached. Thus, in certain embodiments, prior to contacting the polynucleotide-modified substrate and the polynucleotide-modified conjugate component, the method comprises the step of attaching the nucleic acid linker to the substrate to form the polynucleotide-modified substrate. In certain embodiments, prior to contacting the polynucleotide-modified substrate and the polynucleotide-modified conjugate component, the method comprises the step of attaching the nucleic acid linker to the conjugate component to form the polynucleotide-modified conjugate component.

In certain embodiments for producing a polynucleotide-modified bioconjugate, the method comprises contacting a substrate with a conjugate component, wherein the substrate is a binding molecule or a bead, and attaching a nucleic acid linker to the substrate and attaching the same nucleic acid linker to the conjugate component to form the polynucleotide-modified bioconjugate. In certain embodiments, the nucleic acid linker is single-stranded, comprises a double-stranded segment, or the nucleic acid linker is entirely double stranded. In certain embodiments, the nucleic acid linker comprises a double-stranded segment or the nucleic acid linker is entirely double stranded and the method comprises hybridizing nucleic acid strands to form an at least partially double-stranded nucleic acid linker prior to attaching to the substrate and to the conjugate component.

In certain embodiments for producing a polynucleotide-modified bioconjugate, the method comprises contacting a polynucleotide-modified conjugate component comprising a nucleic acid linker with a substrate, wherein the substrate is a binding molecule or a bead, and attaching the nucleic acid linker of the polynucleotide-modified conjugate component to the substrate to form the polynucleotide-modified bioconjugate. In certain embodiments, the nucleic acid linker is single-stranded, comprises a double-stranded segment, or the nucleic acid linker is entirely double stranded. In certain embodiments, the nucleic acid linker is single-stranded (FIG. 18, bottom) In certain embodiments, the nucleic acid linker comprises a double-stranded segment or the nucleic acid linker is entirely double stranded and the method comprises hybridizing nucleic acid strands to form an at least partially double-stranded nucleic acid linker on the polynucleotide-modified conjugate component prior to attaching the nucleic acid linker of the polynucleotide-modified conjugate component to the substrate to form the polynucleotide-modified bioconjugate (FIG. 18, middle).

In certain embodiments for producing a polynucleotide-modified bioconjugate, the method comprises contacting a polynucleotide-modified substrate comprising a nucleic acid linker with a conjugate component, wherein the substrate is a binding molecule or a bead, and attaching the nucleic acid linker of the polynucleotide-modified substrate to the conjugate component to form the polynucleotide-modified bioconjugate. In certain embodiments, the nucleic acid linker is single-stranded, comprises a double-stranded segment, or the nucleic acid linker is entirely double stranded. In certain embodiments, the nucleic acid linker is single-stranded. In certain embodiments, the nucleic acid linker comprises a double-stranded segment or the nucleic acid linker is entirely double stranded and the method comprises hybridizing nucleic acid strands to form an at least partially double-stranded nucleic acid linker on the polynucleotide-modified substrate prior to attaching the nucleic acid linker of the polynucleotide-modified substrate to the conjugate component to form the polynucleotide-modified bioconjugate.

In certain embodiments for producing a polynucleotide-modified bioconjugate, the method comprises contacting (i) a polynucleotide-modified substrate comprising an at least partially or fully single-stranded nucleic acid linker, wherein the substrate is a binding molecule or a bead, (ii) a polynucleotide-modified conjugate component comprising an at least partially or fully single-stranded nucleic acid linker, and (iii) a further at least partially single-stranded nucleic acid linker segment that is not the nucleic acid linker of (i) or (ii). At least a portion of the single-stranded linker sequence of the substrate is complementary to a single-stranded portion of the further nucleic acid linker segment (iii) and/or at least a portion of the single-stranded linker sequence of the conjugate component is complementary to a single-stranded portion of the further nucleic acid linker segment (iii), and thus when contacted, the nucleic acid linker of the substrate, the nucleic acid linker of the conjugate component, and the further nucleic acid linker segment anneal to form an at least partially double-stranded linker linking the substrate to the conjugate component. In certain embodiments, prior to contacting (i), (ii), and (iii), the method comprises the step of attaching the at least partially or fully single-stranded nucleic acid linker to the substrate to form the polynucleotide-modified substrate. In certain embodiments, prior to contacting (i), (ii), and (iii), the method comprises the step of attaching the at least partially or fully single-stranded nucleic acid linker to the conjugate component to form the polynucleotide-modified conjugate component.

For any of the above, methods of attaching a polynucleotide to a molecule such as a protein or antibody are known and include but are not limited to conjugation chemistries such as NHS-esters, maleimides, and "click". Methods of attaching a polynucleotide to a bead are known and include functionalizing the surface of a bead to add a polynucleotide, for example, using the same chemistries described for protein-polynucleotide conjugation. As described elsewhere herein, the DoL of the binding molecule or bead can be stoichiometrically controlled to control the number of polynucleotides attached. As also described in detail elsewhere herein, the nucleic acid linker sequence of the polynucleotide-modified substrate can comprise or consist of polyA, polyT, polyC, and/or polyG sequences and the nucleic acid linker sequence of the modified conjugate component can comprise or consist of polyA, polyT, polyC, and/or polyG sequences. As also described elsewhere herein, the nucleic acid linker can comprise a unique identifying sequence.

Also provided herein is a method of producing a labeled substrate for detection. For illustrative purposes, the substrate is referred to as a binding molecule below but is not limited to a binding molecule. In certain embodiments, the method is a high-rate method. In certain embodiments, separate binding-molecule molecules of the same binding molecule are labeled with different conjugate components. For purposes of the description of such methods (and methods below), "binding molecule" refers to a type of binding molecule, e.g., an anti-CD4 antibody or an anti-beta amyloid antibody, and "binding-molecule molecules" are the individual molecules of that type of binding molecule. For example, in FIG. 4, "$Ab_1$", "$Ab_2$", and "$Ab_n$" are different types of binding molecules, and "$Ab_1$-$N_1$", "$Ab_1$-$N_2$", and "$Ab_1$-$N_m$" are different binding-molecule molecules of the Aby binding molecule (having different labels "$N_1$", "$N_2$", and "$N_m$"). Likewise, "$Ab_2$-$N_1$", "$Ab_2$-$N_2$", and "$Ab_2$-$N_m$" are different binding-molecule molecules of the $Ab_2$ binding molecule having different labels, etc. In certain embodiments, the method comprises: (a) attaching an at least partially or fully single-stranded nucleic acid linker to at least two separate binding-molecule molecules of the same binding molecule to produce a plurality of polynucleotide-modified binding-molecule molecules and then (b) contacting at least one polynucleotide-modified binding-molecule molecule of the plurality with a first polynucleotide-modified conjugate component comprising an at least partially or fully single-stranded nucleic acid linker and contacting at least one different polynucleotide-modified binding-molecule molecule of the plurality with a second polynucleotide-modified conjugate component comprising an at least partially or fully single-stranded nucleic acid linker, wherein the first and second polynucleotide-modified conjugate components comprise detection labels and differ at least in their detection labels. One of ordinary skill in the art would understand that the party conducting step (a) can be separate from the party conducting step (b). Thus, in certain embodiments, the method comprises contacting at least one polynucleotide-modified binding-molecule molecule of the plurality with a first polynucleotide-modified conjugate component comprising an at least partially or fully single-stranded nucleic acid linker and contacting at least one different polynucleotide-modified binding-molecule molecule of the plurality with a second polynucleotide-modified conjugate component comprising an at least partially or fully single-stranded nucleic acid linker, wherein the first and second polynucleotide-modified conjugate components comprise detection labels and differ at least in their detection labels, wherein the plurality of polynucleotide-modified binding-molecule molecules has already been prepared. Consistent with the aspects of this disclosure, at least a portion of the single-stranded nucleic acid linker sequence of the binding-molecule molecules is complementary to a portion of the single-stranded nucleic acid linker sequence of the first and/or second conjugate components and when contacted, the single-stranded nucleic acid linker sequence of the binding-molecules molecules and the single-stranded nucleic acid linker sequence of the conjugate components anneal to form a double-stranded linker linking the binding-molecule molecules to the conjugate components. In certain embodiments, one or more additional polynucleotide-modified binding-molecule molecules of the plurality are contacted with one or more additional polynucleotide-modified conjugate components having different detection labels (e.g., "Ab$_1$-N$_1$", "Ab$_1$-N$_2$", and "Ab$_1$-N$_m$" in FIG. 4). In certain embodiments, at least three, four, five, six, seven, eight, nine, or ten of the polynucleotide-modified binding-molecule molecules of the plurality are each contacted with a polynucleotide-modified conjugate component having a different detection label from the others. In certain embodiments the binding molecule is an antibody or an antigen-binding fragment, variant, or derivative thereof.

One of ordinary skill in the art will understand that in addition to the exemplary high-rate method above, in which the substrate and conjugate component are joined "indirectly" through hybridization of their respective linkers, similar high-rate labeling can be achieved by incorporating any of the various other methods of producing polynucleotide-modified bioconjugates described herein, such that separate binding-molecule molecules of the same binding molecule are labeled with different conjugate components. For example, in certain embodiments, a high-rate method of producing a labeled binding molecule for detection, wherein separate binding-molecule molecules of the same binding molecule are labeled with different conjugate components, comprises (a) obtaining a plurality of binding-molecule molecules of the same binding molecule and (b) attaching the nucleic acid linker of a first polynucleotide-modified conjugate component to at least one binding-molecule molecule of the plurality and attaching the nucleic acid linker of a second polynucleotide-modified conjugate component to at least one different binding-molecule molecule of the plurality, wherein the first and the second polynucleotide-modified conjugate components comprise detection labels and differ at least in their detection labels, such that separate binding-molecule molecules of the same binding molecule are labeled with different conjugate components. The nucleic acid linkers can be single-stranded, comprise a double-stranded segment, or is entirely double stranded. In certain embodiments, the nucleic acid linker comprises a double-stranded segment or the nucleic acid linker is entirely double stranded, and the method comprises hybridizing nucleic acid strands to form an at least partially double-stranded nucleic acid linker prior to attaching the nucleic acid linker of the polynucleotide-modified conjugate component to the binding-molecule molecule to form the polynucleotide-modified binding molecule bioconjugate. In certain embodiments, one or more additional binding-molecule molecules of the plurality are attached to one or more additional polynucleotide-modified conjugate components having different detection labels. In certain embodiments, at least three, four, five, six, seven, eight, nine, or ten of the binding-molecule molecules of the plurality are each contacted with a polynucleotide-modified conjugate component having a different detection label from the others. And, in certain embodiments, the binding molecule is an antibody or an antigen-binding fragment, variant, or derivative thereof.

In order to achieve separate labeling, certain embodiments comprise distributing, aliquoting, or the like, binding-molecule molecules or polynucleotide-modified binding-molecule molecules of the plurality into separate compartments for contacting with a uniquely labeled polynucleotide-modified conjugate components in each compartment, thus producing differently-labeled binding-molecule molecules of the same binding molecule. One of ordinary skill in the art would understand that the distribution/aliquoting could be done manually such as pipetting reagents into separate tubes, or by a system such as an automated fluid handler that could aliquot reagents at a high-rate into a large number of bottles, or separate wells of a tissue-culture type plate, or other containers.

One significant advantage of such a method is that it can reduce the requirement for the design, production, organization, storage, etc., of multiple linker molecules. In certain embodiments, the at least partially or fully single-stranded nucleic acid linker of the plurality of the binding-molecule molecules is the same for all of the polynucleotide-modified binding-molecule molecules and thus the at least partially or fully single-stranded nucleic acid linker of the conjugate component can also be the same for all the polynucleotide-modified conjugate-components.

Figure 4:
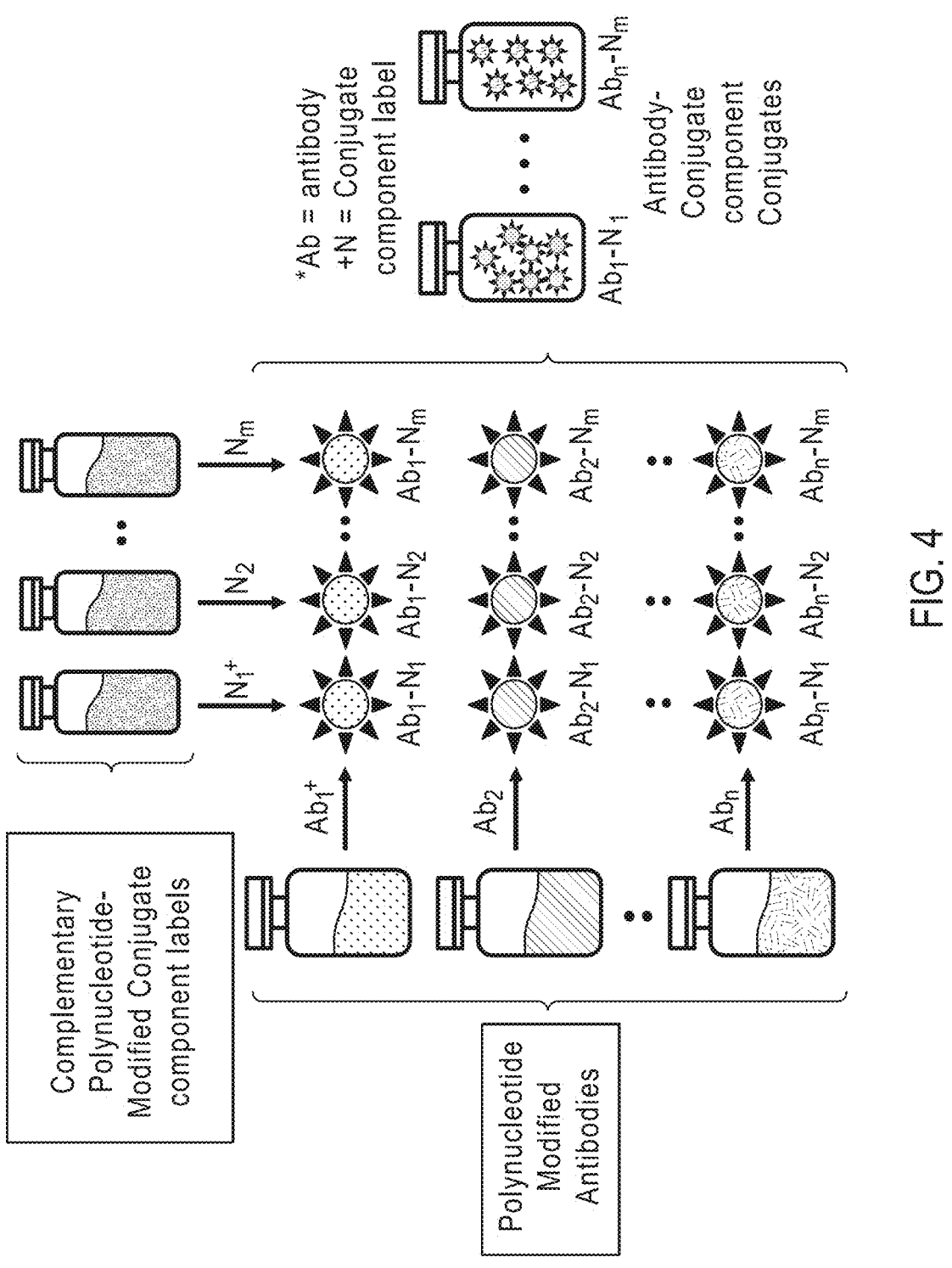
FIG. 4 shows a high-rate method of producing the same antibody labeled with different labels, different antibodies labeled with the same label, and different antibodies labeled with different labels.

Similarly, provided herein is a method of producing labeled binding molecules for detection, however, wherein different binding molecules are labeled with the same conjugate component (but not the same conjugate-component molecule). This is illustrated in FIG. 4, e.g., "Ab$_1$-N$_1$", "Ab$_2$-N$_1$", and "Ab$_n$-N$_1$" are different binding molecules ("Ab$_1$", "Ab$_2$", and "Ab$_n$") labeled with same label ("N$_1$"). In certain embodiments, the method is a high-rate method. In certain embodiments, the method comprises: (a) attaching an at least partially or fully single-stranded nucleic acid linker to at least two different binding molecules to produce at least two different polynucleotide-modified binding molecules and (b) contacting the at least two different polynucleotide-modified binding molecules with a polynucleotide-modified conjugate component comprising a detection label and comprising an at least partially or fully single-stranded nucleic acid linker. As noted above, one of ordinary skill in the art would understand that the party conducting step (a) can be separate from the party conducting step (b). Thus, in certain embodiments, the method comprises contacting at least two different polynucleotide-modified binding molecules with a polynucleotide-modified conjugate component comprising a detection label and comprising an at least partially or fully single-stranded nucleic acid linker. Consistent with the aspects of this disclosure, at least a portion of the single-stranded nucleic acid linker sequence of the binding molecules is complementary to a portion of the single-stranded nucleic acid linker sequence of the conjugate component and when contacted, the linkers anneal to form a double-stranded linker linking the binding molecules to the conjugate component. In certain embodiments, one, two, three, four, five, six, seven, eight, nine, ten, or more additional polynucleotide-modified binding molecules are contacted with the polynucleotide-modified conjugate component. In certain embodiments, one or more of the binding molecules is an antibody or an antigen-binding fragment, variant, or derivative thereof.

One of ordinary skill in the art will understand that in addition to the exemplary high-rate method above, in which the substrate and conjugate component are joined "indirectly" through hybridization of their respective linkers, similar high-rate labeling can be achieved by incorporating any of the various other methods of producing polynucleotide-modified bioconjugates described herein, such that different binding molecules are labeled with the same conjugate component. For example, a high-rate method of producing labeled binding molecules for detection, wherein different binding molecules are labeled with the same conjugate component, comprises (a) obtaining at least two different binding molecules and (b) attaching the at least two different binding molecules to the nucleic acid linker of a polynucleotide-modified conjugate component comprising a detection label, such that different binding molecules are labeled with the same conjugate component. The nucleic acid linker can be single-stranded, comprise a double-stranded segment, or is entirely double stranded. In certain embodiments, the nucleic acid linker comprises a double-stranded segment or the nucleic acid linker is entirely double stranded and the method comprises hybridizing nucleic acid strands to form an at least partially double-stranded nucleic acid linker prior to attaching the nucleic acid linker of the polynucleotide-modified conjugate component to the binding-molecules to form the polynucleotide-modified binding molecule bioconjugate. In certain embodiments, one, two, three, four, five, six, seven, eight, nine, ten, or more additional binding molecules are attached to the polynucleotide-modified conjugate component. And, in certain embodiments, the one or more of the binding molecules is an antibody or an antigen-binding fragment, variant, or derivative thereof.

Certain embodiments comprise distributing, aliquoting, or the like (as described elsewhere herein) the different binding molecules or polynucleotide-modified binding molecules into a separate compartment for each type of binding molecule for contacting with the polynucleotide-modified conjugate component in each compartment, thus producing different binding molecules labeled with the same conjugate component label.

In certain embodiments, the at least partially or fully single-stranded nucleic acid linker of the different binding molecules is the same for all the polynucleotide-modified binding molecules and a single at least partially or fully single-stranded nucleic acid sequence can be used as the nucleic acid linker of the polynucleotide-modified conjugate component.

Further the methods described above can be combined in a method of producing a labeled binding molecule or binding molecules for detection in numerous different combinations. In certain embodiments, the method of creating different combinations uses one or just a few nucleic acid linker sequences. In certain embodiments, the method is a high-rate method. For example, in certain embodiments, different conjugate component labels can be "printed" onto binding molecules (or other substrates disclosed herein) in a high-rate manner for production.

In certain embodiments, the process of making a polynucleotide-modified bioconjugate of the disclosure involves contacting components together, as described elsewhere herein, so that the complementary portions of the single-stranded component linkers can anneal to form an at least partially double-stranded linker linking the components into the bioconjugate. The components can be contacted with each other in a composition. For example, in certain embodiments, the composition can be a solution. In certain embodiments, the composition comprises a substrate comprising (a) an at least partially or fully single-stranded nucleic acid linker and (b) a conjugate component comprising an at least partially or fully single-stranded nucleic acid linker. In certain embodiments, the substrate is a binding molecule or a bead. As previously noted, in certain embodiments at least a sufficient portion of the sequence of the single-stranded nucleic acid linker sequence of the substrate is complementary to a portion of the single-stranded nucleic acid linker sequence of the conjugate component to allow for the nucleic acid linkers to anneal and form a double-stranded nucleic acid linker linking the substrate to the conjugate component. In certain embodiments, the composition comprises (a) a substrate comprising a nucleic acid linker, wherein the substrate is a binding molecule or a bead and (b) a conjugate component capable of attachment to the nucleic acid linker to link the substrate to the conjugate component. In certain embodiments, the nucleic acid linker is single-stranded, comprises a double-stranded segment, or the nucleic acid linker is entirely double stranded. In certain embodiments, the composition comprises (a) a conjugate component comprising a nucleic acid linker and (b) a substrate capable of attachment to the nucleic acid linker to link the conjugate component to the substrate. In certain embodiments, the nucleic acid linker is single-stranded, comprises a double-stranded segment, or the nucleic acid linker is entirely double stranded. In certain embodiments, the composition comprises (a) a substrate capable of attachment to a nucleic acid linker, wherein the substrate is a binding molecule or a bead, and a conjugate component capable of attachment to a nucleic acid linker, and (b) a nucleic acid linker. In certain embodiments, the nucleic acid linker is single-stranded, comprises a double-stranded segment, or the nucleic acid linker is entirely double stranded. In certain embodiments, the composition comprises (a) a substrate comprising an at least partially or fully single-stranded nucleic acid linker, wherein the substrate is a binding molecule or a bead, (b) a conjugate component comprising an at least partially or fully single-stranded nucleic acid linker; and (c) a further nucleic acid linker segment, wherein (v)(a), (v)(b), and (v)(c) can anneal to form an at least partially double-stranded nucleic acid linker comprising (v)(a), (v)(b), and (v)(c) and linking (v)(a) to (v)(b).

In certain embodiments of any of the above, the composition is capable of producing the polynucleotide-modified binding molecule bioconjugate or the polynucleotide-modified bead bioconjugate disclosed anywhere herein.

Another aspect of this disclosure is a method of labeling a cell, tissue, and/or organ. In certain embodiments, the cell, tissue, and/or organ is normal or healthy. In certain embodiments, the cell, tissue, and/or organ is for example, abnormal, diseased, or damaged. For example, in certain embodiments, the cell and/or tissue is a cancer cell or tumor. In certain embodiments, the method comprises contacting the cell, tissue, and/or organ with a polynucleotide-modified binding molecule bioconjugate disclosed herein, wherein the binding molecule portion of the bioconjugate binds to an antigen, epitope, and/or hapten of the cell, tissue, and/or organ and wherein the conjugate component portion comprises a detectable label, such as a dye. In certain embodiments, the binding molecule portion of the bioconjugate specifically recognizes and specifically binds to an antigen, epitope, and/or hapten of the cell, tissue, and/or organ. In certain embodiments, the method comprises contacting the cell, tissue, and/or organ with a polynucleotide-modified binding molecule bioconjugate disclosed herein, wherein the binding molecule portion of the bioconjugate binds to a receptor on or in the cell, tissue, and/or organ and wherein the conjugate component portion comprises a detectable label, such as a dye. In certain embodiments, the binding molecule portion of the bioconjugate specifically recognizes and specifically binds to a receptor on or in the cell, tissue, and/or organ. In certain embodiments, the label is a label for visual detection. In certain embodiments, the label is an oligonucleotide-based fluorescent label such as a PHITON. Such labeling can be used for numerous applications. Representative examples include wherein the labeled cell can be used for one or more of flow cytometry, antibody screening, ELISA or other sandwich assays, immune monitoring, bio-marker assays, lateral flow, point-of-care/rapid diagnostics, imaging, microscopy, molecular diagnostics, next genera-tion sequencing, long read sequencing, in situ sequencing, polymerase chain reaction, microarrays, nucleic acid sequencing, amino acid sequencing, digital pathology, Southern blotting, Northern blotting, Western blotting, or prophylactic and/or therapeutic purposes. For example, in certain embodiments, the labeled cell is used in flow cytom-etry. Further, in certain embodiments, the label is a label for cellular membranes, for example, wherein a lipophilic moi-ety is attached to a label enabling it to stain cellular membranes, or alternatively, incorporating a myristoylation/palmitoylation sequence into or attached to a label, or alternatively, by conjugation to lectins, e.g., Wheat germ agglutinin (WGA) to detect glycoconjugates on cell mem-branes. In certain embodiments, the label is a label for cellular viability, for example, by conjugation to probes specific for double-stranded DNA (DNA binding, as DNA is accessible in dead cells), or alternatively by attaching the label to an amine-reactive moiety (which will react with many of the intracellular proteins of dead cells and enable their identification and or exclusion from analysis). In cer-tain embodiments, the label is attached to enzyme activated moieties which enable the staining and passage to daughter cells of an intracellular label. In certain embodiments, the label is a specific label targeting genomic material, for example, bound or alternatively containing a sequence that enables it to bind to a unique sequence RNA or DNA (e.g. through FISH or other imaging or fluorescence measure-ments modalities).

Also provided for are methods and reagents for quanti-tatively measuring a signal from a labeled cell, tissue, and/or organ. In certain embodiments, the method comprises con-tacting the cell, tissue, and/or organ with a polynucleotide-modified binding molecule bioconjugate disclosed herein—wherein the binding molecule portion of the bioconjugate binds to an antigen, epitope, membrane, genomic material, and/or hapten of the cell, tissue, and/or organ and the conjugate component portion comprises a detectable label—and measuring the presence of the polynucleotide-modified binding molecule bioconjugate, wherein the DoL is known, thus allowing a quantitative measurement to be made. In certain embodiments, the method comprises contacting the cell, tissue, and/or organ with a polynucleotide-modified binding molecule bioconjugate disclosed herein—wherein the binding molecule portion of the bioconjugate binds to a receptor on or in the cell, tissue, and/or organ and the conjugate component portion comprises a detectable label—and measuring the presence of the polynucleotide-modified binding molecule bioconjugate, wherein the DoL is known, thus allowing a quantitative measurement to be made. In certain embodiments, the label is a label for visual detection. In certain embodiments, the label is an oligonucleotide-based fluorescent label such as a PHITON. In certain embodiments, the degree-of-labeling (DoL) of the binding molecule is controlled stoichiometrically via the availability of the nucleic acid. In certain embodiments, the DoL of the biding molecule is 1, 2, 3, 4, 5, 6, 7, 8, 9, or 10 or any range in between inclusive of the endpoints. In certain embodi-ments, the degree-of-labeling (DoL) of the nucleic acids on a polynucleotide-modified binding molecule is 1, 2, 3, 4, 5, 6, 7, 8, 9, 10, or 11, or any range in-between inclusive of the endpoints and is independent of the DoL of the conjugate component. And in certain embodiments, a control comprising a polynucleotide-modified bead bioconjugate, such as with a known DoL, can be utilized to aid in the quantifica-tion.

Also provided herein are kits for producing and/or using a polynucleotide-modified bioconjugate of this disclosure. In certain embodiments, a kit comprises one or more com-ponents necessary to produce the polynucleotide-modified bioconjugate of this disclosure. In certain embodiments, a kit comprises one or more components necessary to produce a composition of this disclosure. In certain embodiments, a kit comprises one or more components necessary to label a substrate in a high-rate method of this disclosure, to label a cell, tissue, and/or organ, and/or to perform quantitative analysis as provided herein. For example, in certain embodi-ments a kit comprises one or more of substrates such as binding molecules (e.g., antibodies and derivatives) or beads, conjugate components, single-stranded, partially single-stranded/partially double-stranded, or fully double-stranded nucleic acid linkers, polynucleotide-modified sub-strates, polynucleotide-modified conjugate components, and/or polynucleotide-modified bioconjugates. In certain embodiments, the kit further comprises instructions for performing any method disclosed herein, either printed and/or on an electronic storage medium, buffers and/or additional reagents, and/or packaging materials.

Beads.

One of ordinary skill in the art will be familiar with many types of polystyrene microspheres. Polystyrene micro-spheres are highly uniform with respect to both size and fluorescence intensity. They are designed to approximately replicate the size, emission wavelength and intensity of biological samples. In certain cases, because dyes can be contained inside the microsphere's matrix instead on the surface, the beads have excellent photochemical and physi-cal stability, providing reliable reference signals for align-ing, focusing and calibrating flow cytometers (e.g., Align-Flow, ThermoFisher). Such fluorescent dyes are selected for optimal excitation by laser sources commonly used in flow cytometry such as in the 2.5 μm-diameter and 6.0 μm-di-ameter range. In another example (BD Cytometry Setup and Tracking (CS&T) Beads), equal concentrations of three polystyrene beads differ in relative intensity: dim, midrange, and bright. All three beads have a low intrinsic CV and contain dyes spanning a wide range of both excitation and emission wavelengths used in many flow cytometry appli-cations. Some other examples of beads are antibody capture beads: These beads capture antibodies and can serve as controls for fluorescence compensation (e.g., OneComp and UltraComp eBeads: polystyrene microspheres; AbC Total Antibody and ArC Amine-Reactive Compensation Bead: polystyrene microspheres). Other examples of beads include: counting beads; sterile technique beads (e.g., "GloGerm bead"); Polyscience Yellow-Green (YG) bead, which are a highly fluorescent and uniform particle available from 0.5 μm to 10 μm; and quantification beads. Another example includes Quantum MESF beads (PE labeled anti-bodies), which are well-characterized beads. The F/P ratio for PE is generally 1:1, due to steric constraints.

Quantitation.

Currently, flow cytometry measurement and other fluo-rescence-based measurement and diagnostic modalities are relative. That is, measurements are made relative to a control rather than getting the true number of molecules (e.g. proteins) on a per cell basis such as in flow cytometry. Efforts have been made to create quantitative standards for flow cytometry but are limited to a single dye (phycoerythrin) due to the labeling variability of antibodies as described herein.

The degree-of-loading (DoL) of a dye on a binding molecule such as an antibody (i.e., the number of dyes per antibody) changes the brightness of the label. Due to the variance in typical conjugation strategies the DoL has a distribution across all binding molecules and so does the brightness. The only method to alleviate this variation in DoL is to reduce the concentration of dyes to achieve a 1:1 labeling. However, reactions at this low of a concentration suffer from low yields and produce many antibodies with no dyes and a few with one dye. This makes it impractical to create quantitative, labeled antibodies that are also bright enough to be useful. Further, traditional conjugation strategies require extensive post-reaction cleanup to remove side products, inactivated dyes, and unlabeled antibody.

Figure 5:
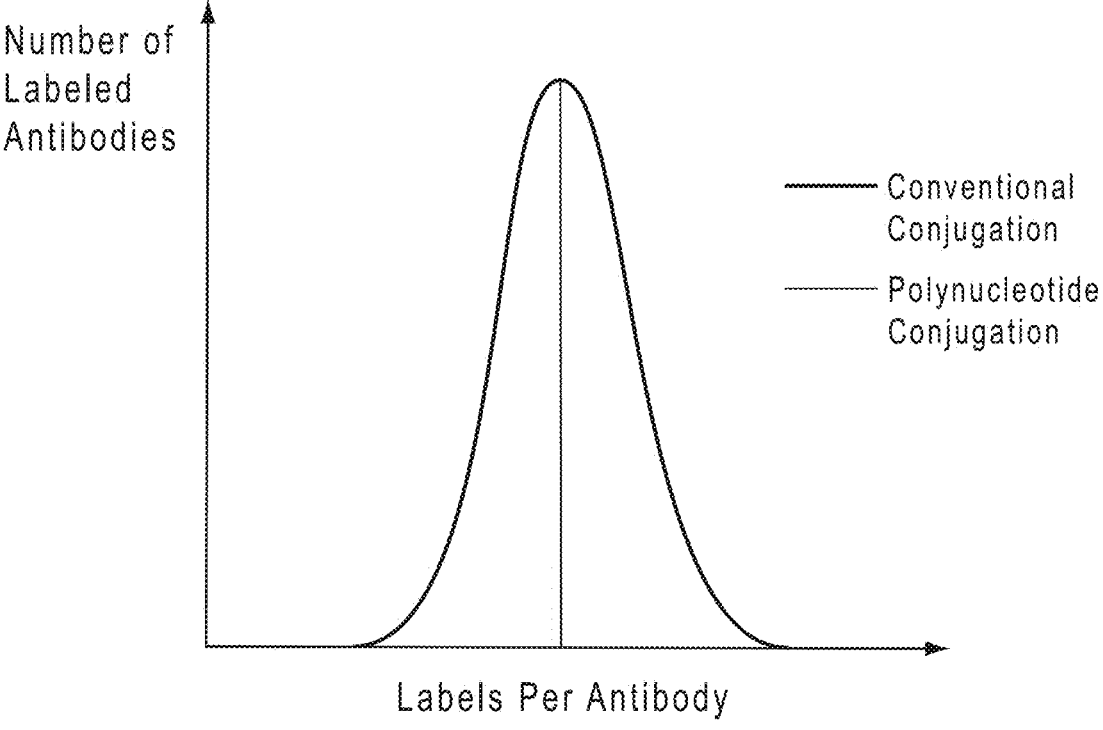
FIG. 5 shows a comparison of the distribution of labels per antibody obtained by conventional conjugation methods in comparison to methods of this disclosure.

The nucleic acid linker system of this disclosure enables the quantitative analysis of labeled bioconjugates by leveraging 1:1 DoL. FIG. 5 illustrates the difference between traditional conjugation strategies and the nucleic acid/polynucleotide linkers described herein. FIG. 5 shows the number of labeled antibodies versus the labels per antibody. The curve represents the distribution typically encountered with traditional conjugation methods and the 'delta' function in the middle represents what polynucleotide linkers can produce.

Figure 6:
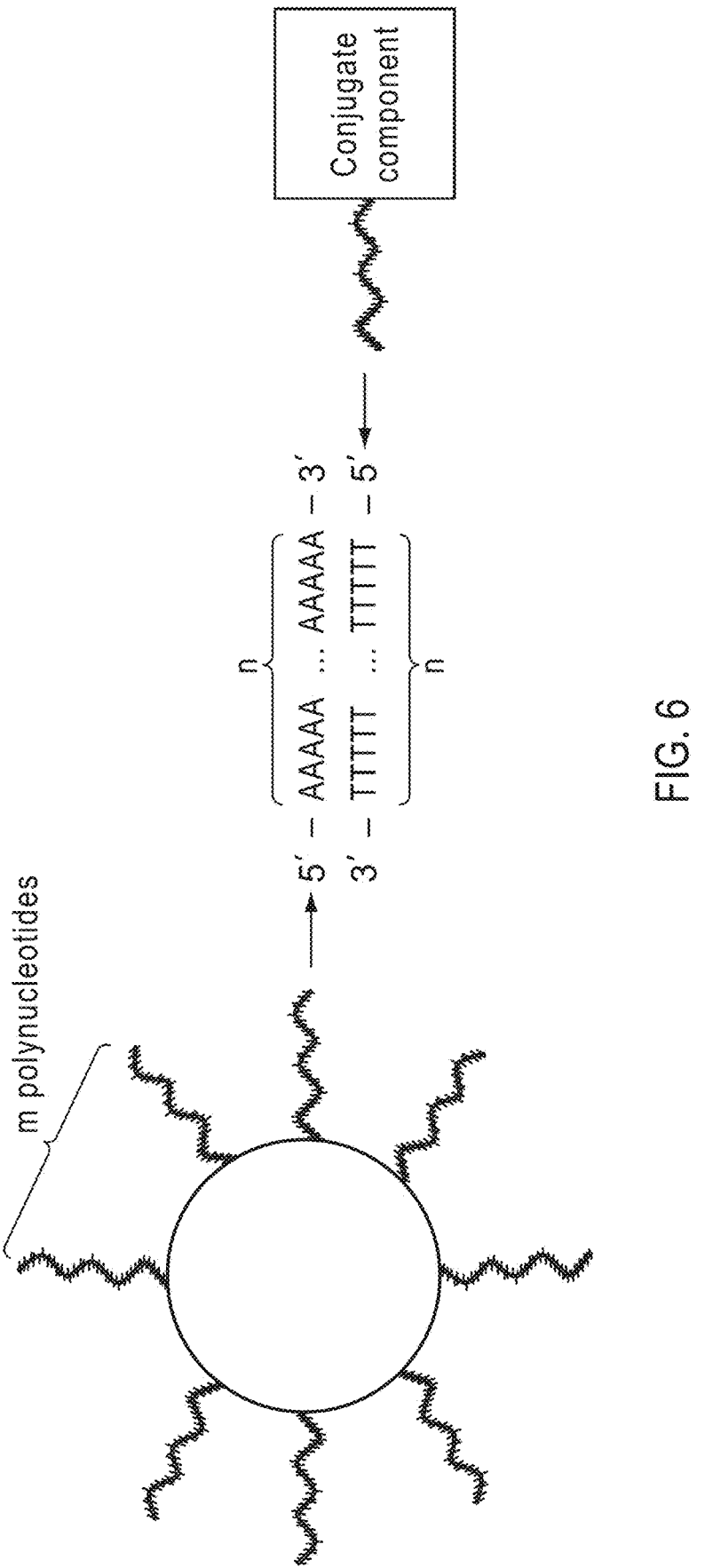
FIG. 6 shows an illustrative example of the component parts of a polynucleotide-modified bead bioconjugate of this disclosure (a polynucleotide-modified bead, a double-stranded polynucleotide linker with complementary polyA and polyT nucleic acid strands, and a polynucleotide-modified conjugate component).

The control of DoL makes it possible to directly measure the number of proteins on a cell surface by comparing the observed fluorescence to a working curve generated by analyzing a series of specialized microspheres/beads loaded with "m" polynucleotide (e.g., polyA). FIG. 6 illustrates the concept of a PHITON (oligonucleotide-based fluorescent label) with a polyT linker segment captured by annealing to the polyA linker segment of a bead. The beads can then be washed and purified by centrifugation to yield a population of beads with a constant DoL, within the variability of the bead diameter.

Figure 7:
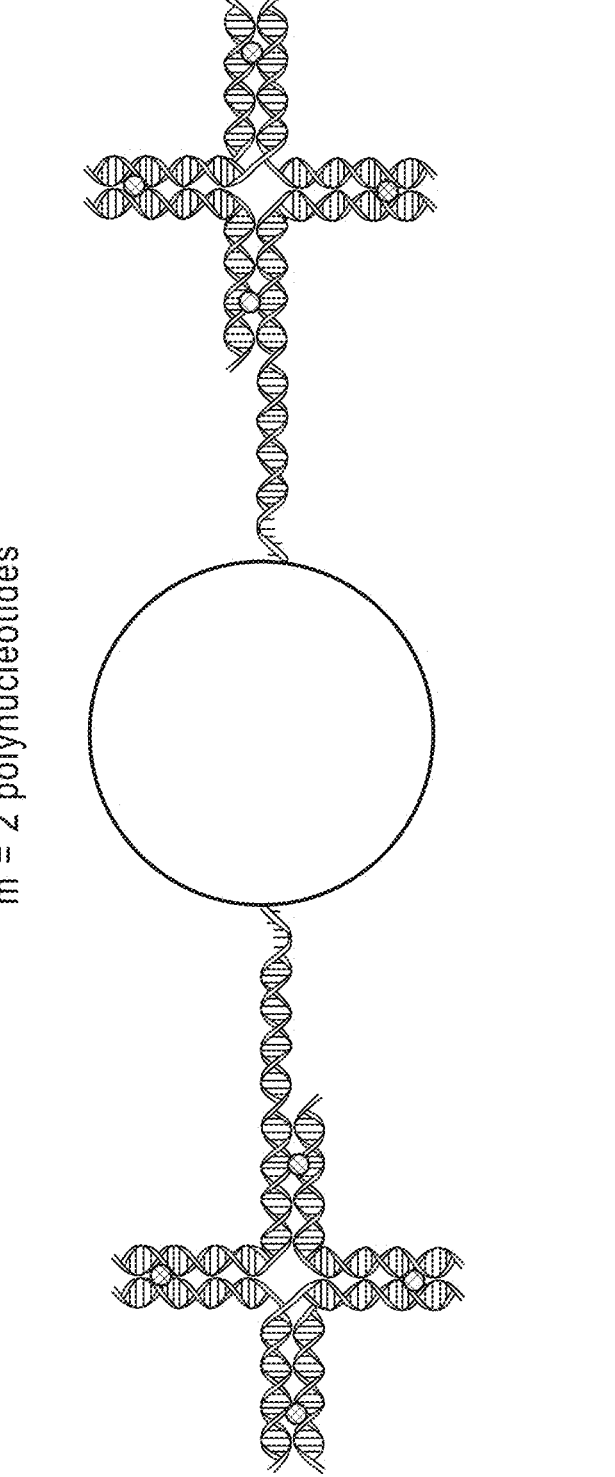
FIG. 7 shows an illustrative example of a polynucleotide-modified bead bioconjugate of this disclosure comprising a bead and two oligonucleotide-based fluorescent labels linked to the bead via polynucleotide linkers.

FIG. 7 illustrates how the number ("m") of linkers on the bead can vary and capture the same number of PHITONS in a 1:1 fashion.

Figure 8A:
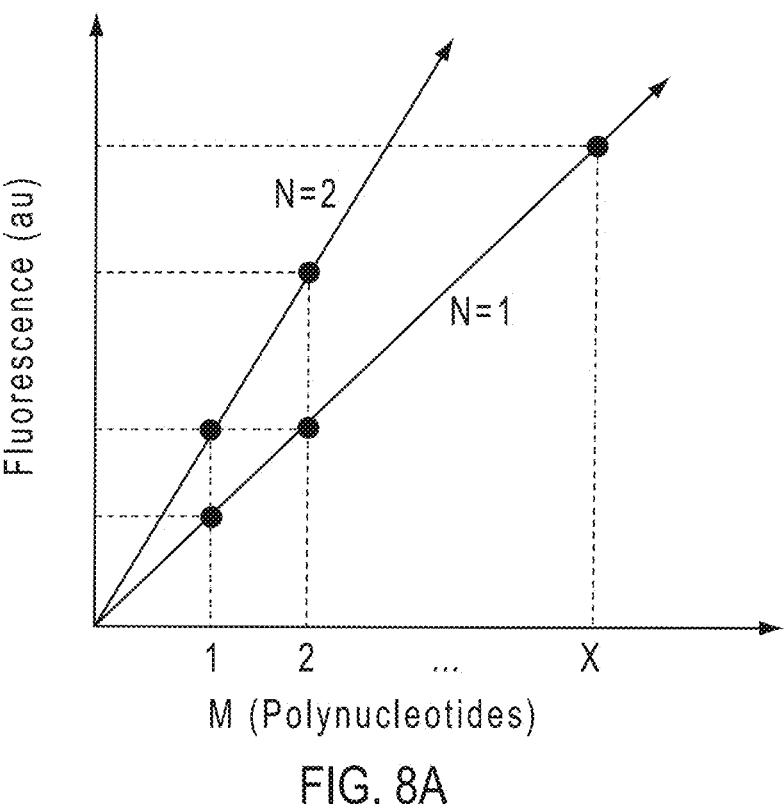
FIGS. 8A and 8B show how by controlling the number of labels/dyes attached to a bead, quantitative measurements can be made.
Figure 8B:
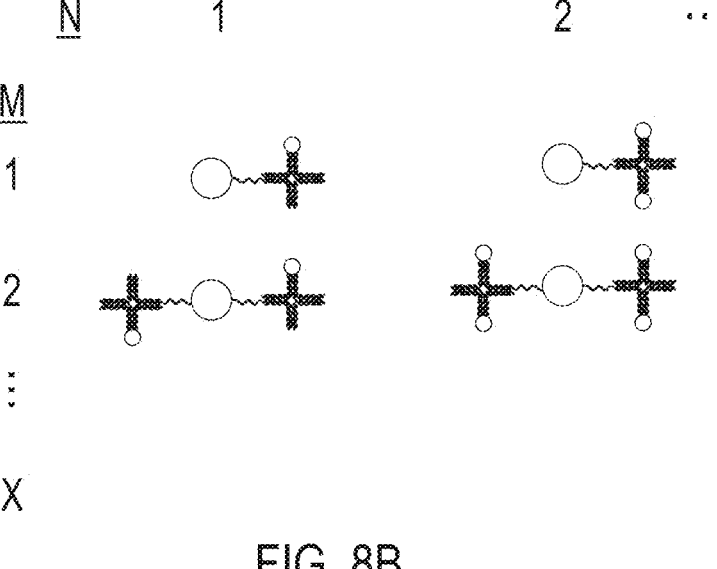

FIGS. 8A-8B illustrate how beads with varying numbers of polynucleotides (e.g., polyT) on their surface ("m") and the brightness of the attached PHITON ("n") linearly changes their fluorescence. For example, FIG. 8A shows two lines that represent two PHITONS, n=1 cluster and n=2 clusters. Their slopes are different because for each marginal increase in the linker count per bead ("m"), the fluorescence increases by a larger amount since an n=2 clusters PHITON fluoresces 2× more than an n=1 cluster PHITON.

With a sufficient number of values for (m,n) it is possible to use linear regression to determine the number of dye molecules linked to a surface (e.g., bead, cell, etc.) based on the fluorescence signal. Further, quantitation with such dye-labeled beads can provide important insight into the limits of detection for a system, i.e., how small of a signal can it detect. This could also be used to determine the sensitivity of any 3' based RNA detection modality that relies on the polyA tail.

Thus, the conjugation process provided herein reduces the variability associated with other techniques, and enables finely tuned control of the number of dye molecules (e.g., oligo-based dyes) or any other molecules that are being conjugated to a binding molecule. With a known amount of dye and a known, well-characterized fluorescence from each of these dyes, a truly quantitative system is disclosed. Critically, in setting up a standard curve in this well-controlled system (see FIGS. 8A-8B), the number of bioconjugates, e.g., on the surface of a cell in flow cytometry, can quantitatively be determined. This can be done simultaneously on a single cell, enabling not just the first true quantitation in flow cytometry but also the ability to do this across multiple bioconjugates at the same time, on a single-cell basis.

Compensation.

Due to the overlap between the emission spectra between different fluorophores, compensation (also called unmixing in other fields of study) is used. The goal of compensation is to remove the spillover fluorescence of a particular probe from the "wrong" channel. For example, fluorescein fluorescence is primarily green, which is measured in the FL1 (FITC) channel, but fluorescein also has a significant yellow component to the fluorescence, which appears in the FL2 (PE) channel. In current practice, cells are stained with antibodies having the same dyes that are used experimentally or anti-antibody beads. Single stain controls are conducted to determine the off-channel fluorescence and a compensation matrix is created to account for this. This has recently been extended to spectral compensation, which is an overdetermined system (i.e. more detectors than fluorophores) but the underlying approach is similar.

Tandem dyes (i.e., those made up of 2 fluorophores like PE-Cy7 or APC-Cy7 and can rely on FRET for fluorescence) increase the requirements in compensation. Use of these tandem dyes puts a burden on the researcher, as the FRET interaction of these dyes change when bound to different antibodies. This necessitates running the exact antibody with FRET pair used experimentally in single stain compensation controls, and leads to one compensation matrix per panel that contains one of these tandems. Table 2, for example, shows four difference four color panels.

TABLE 2

| CD1-FITC | CD1-FITC | CD1-FITC | CD1-FITC |
|---|---|---|---|
| CD2-PE | CD2-PE | CD2-PE | CD2-PE |
| CD3-PerCP | CD3-PerCP | CD3-PerCP | CD3-PerCP |
| CD4-PE-Cy7 | CD5-PE-Cy7 | CD6-PE-Cy7 | CD7-PE-Cy7 |

The antibody nomenclature used in Table 2 is shorthand, e.g., CD3-PE is short for anti-CD3 antibody conjugated to phycoerythrin).

The fluorescence properties are different between CD4-PE-Cy7, CD5-PE-Cy7, CD6-PE-Cy7, and CD7-PE-Cy7, necessitating four different compensation matrices in this experiment (one per panel) and 7 different compensations to be run (Table 3):

TABLE 3

| CD1-FITC |
|---|
| CD2-PE |
| CD3-PerCP |
| CD4-PE-Cy7 |
| CD5-PE-Cy7 |
| CD6-PE-Cy7 |
| CD7-PE-Cy7 |

In certain embodiments of this disclosure, however, gentler conjugation protocols and the characteristics of conjugating a DNA-based platform which stabilizes both single species and multiple species (FRET) dyes, the optical properties of dye-conjugated antibodies (e.g., PHITON-conjugated antibodies) does not change. This enables the same experiment to be run with one compensation matrix and four compensation controls. For example, using PHITON-conjugated antibodies, the experiment would be:

TABLE 4

| | | | |
|---|---|---|---|
| CD1-FITC | CD1-FITC | CD1-FITC | CD1-FITC |
| CD2-PE | CD2-PE | CD2-PE | CD2-PE |
| CD3-PerCP | CD3-PerCP | CD3-PerCP | CD3-PerCP |
| CD4-NY610 | CD5-NY610 | CD6-NY610 | CD7-NY610 |

All four panels would (and could validly) share one compensation matrix, and would only require the running of four compensation controls, thus vastly simplifying experimental design.

Figure 9A:
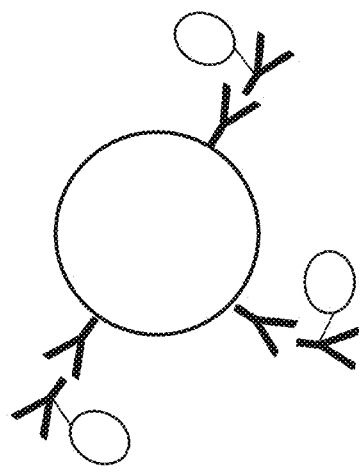
FIGS. 9A and 9B show traditional control beads (left) and the PHITON label-embedded and/or externally labeled beads.
Figure 9B:
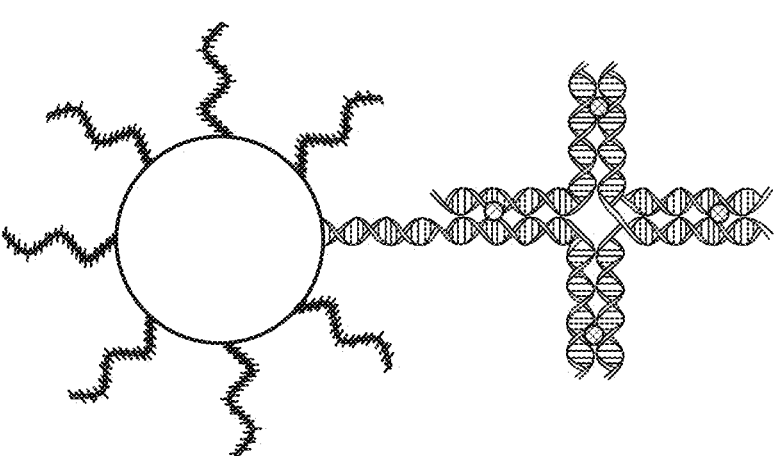

Using such a system, one of ordinary skill in the art can use polynucleotide-modified beads conjugated via a nucleic acid linker to polynucleotide-modified dyes having a nucleic acid linker with a corresponding (complementary) sequence, without the need for antibodies (FIGS. 9A-9B). These compensation controls are a consistent method for running single stain controls. In addition, as they are not subject to the distribution of dye molecules on an antibody (i.e., they are just pure dye on a bead, which can both be quantitated), the inherent measurement noise of the single stain control itself is minimized.

Thus, as discussed above, conjugation methods of this disclosure enable the placement of dyes directly onto beads, avoiding the cost associated with using dye-conjugated antibodies for compensation controls. Such methods also avoid the variability that occurs and multiplication of compensation matrices (as each tandem-conjugated antibody behaves differently and this requires its own compensation control). Certain embodiments enable users to run one consistent set of multicolor controls (for example, oligo-based dyes conjugated directly to beads).

Purification.

Figure 3:
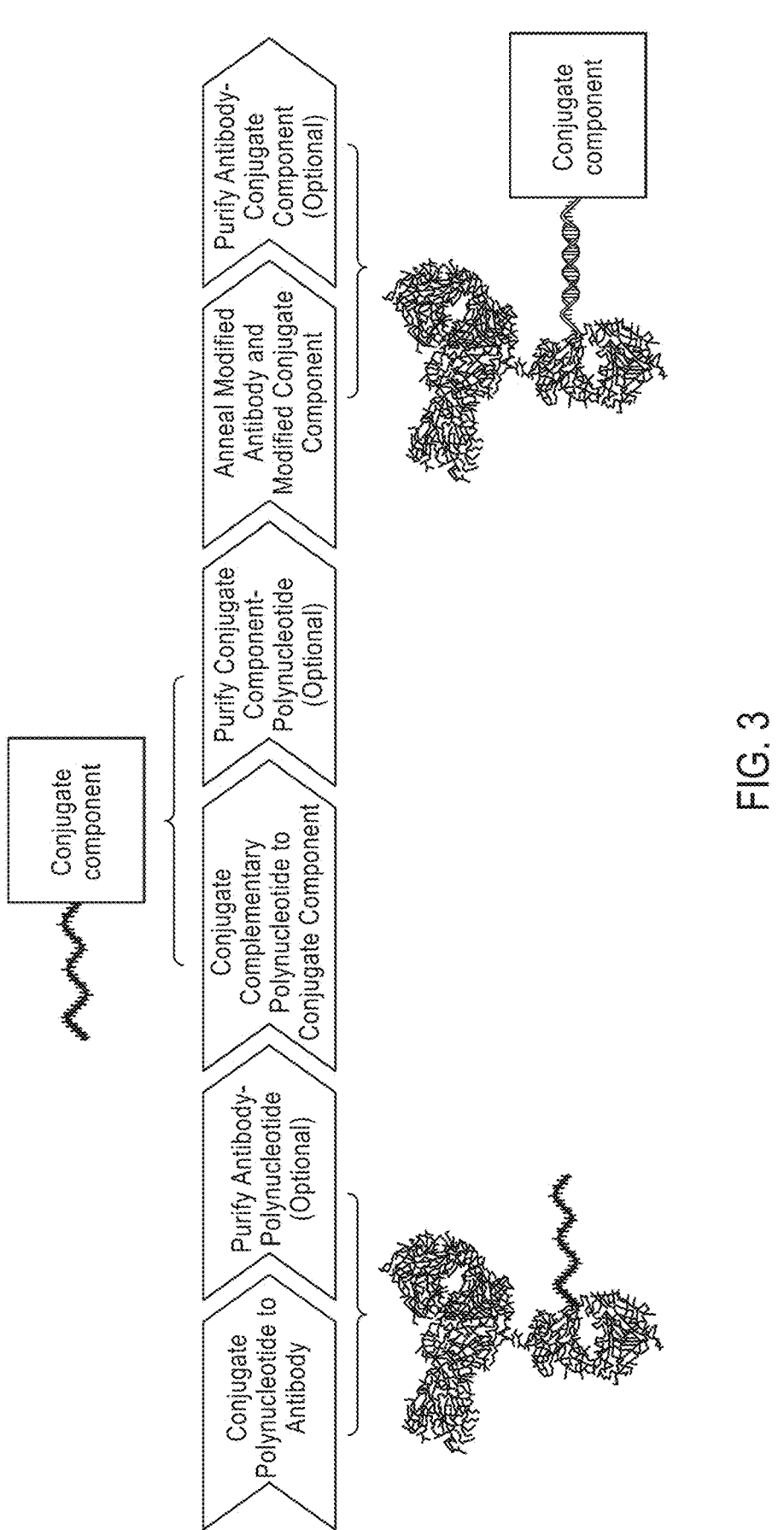
FIG. 3 illustrates a method for producing a polynucleotide-modified antibody bioconjugate of this disclosure.
Figure 10:
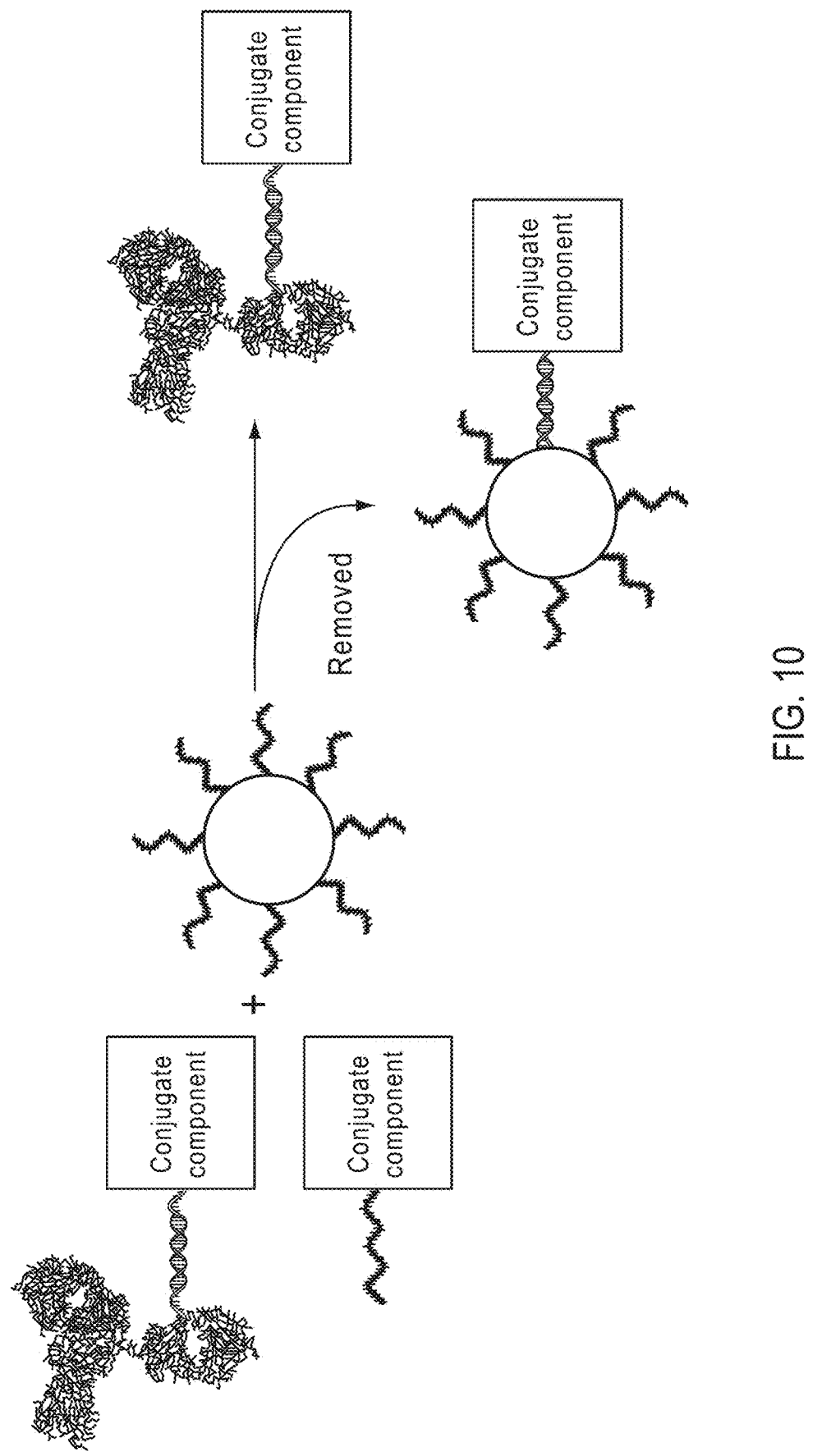
FIG. 10 illustrates a method of purification by removing excess polynucleotide-modified conjugate components not linked to polynucleotide-modified antibodies by annealing the single-stranded nucleic acid linker portion of the excess polynucleotide-modified conjugate components to complementary nucleic acid strands bound to a bead.

While for reasons discussed elsewhere herein, purification may not be necessary, the methods of producing bioconjugates of this disclosure allow for the purification of free dye or other conjugate components, for example in the case where high purity bioconjugates are a requirement (See, e.g., FIG. 3 and FIG. 10). For example, if conjugation were to be used to create drug-antibody bioconjugates, the method would also enable the purification of both unbound antibody and drug in a GMP manufacturing process.

In certain embodiments, polynucleotide-modified substrates, such as binding molecules and/or conjugate components, such as an polynucleotide-based labels, can be captured from a composition comprising polynucleotide-modified bioconjugates comprising annealed double-stranded linkers, by annealing the single-stranded linker region of the polynucleotide-modified substrate and/or polynucleotide modified conjugate components to a nucleic acid strand having an at least partially complementary sequence. In certain embodiments, the nucleic acid strand having the complementary sequence is attached to a bead or to a surface for purification. In certain embodiments, after the single-stranded linker region of the polynucleotide-modified substrate and/or polynucleotide modified conjugate component is linked to the bead, the bead is separated from the polynucleotide-modified bioconjugates, such as by removal by centrifugation. In certain embodiments, the polynucleotide-modified bioconjugate is separated by passing the components over the immobilized nucleic acid having the complementary sequence. In certain embodiments, a bead could serve as both a bead and an immobilized surface such as beads siting in a chromatography column.

In certain embodiments, the method produces a waste product (e.g., unbound, removed conjugate) that can be recycled by displacing the linkage with the conjugate.

Oligonucleotide-Based Fluorescent Labels.

Figure 14:
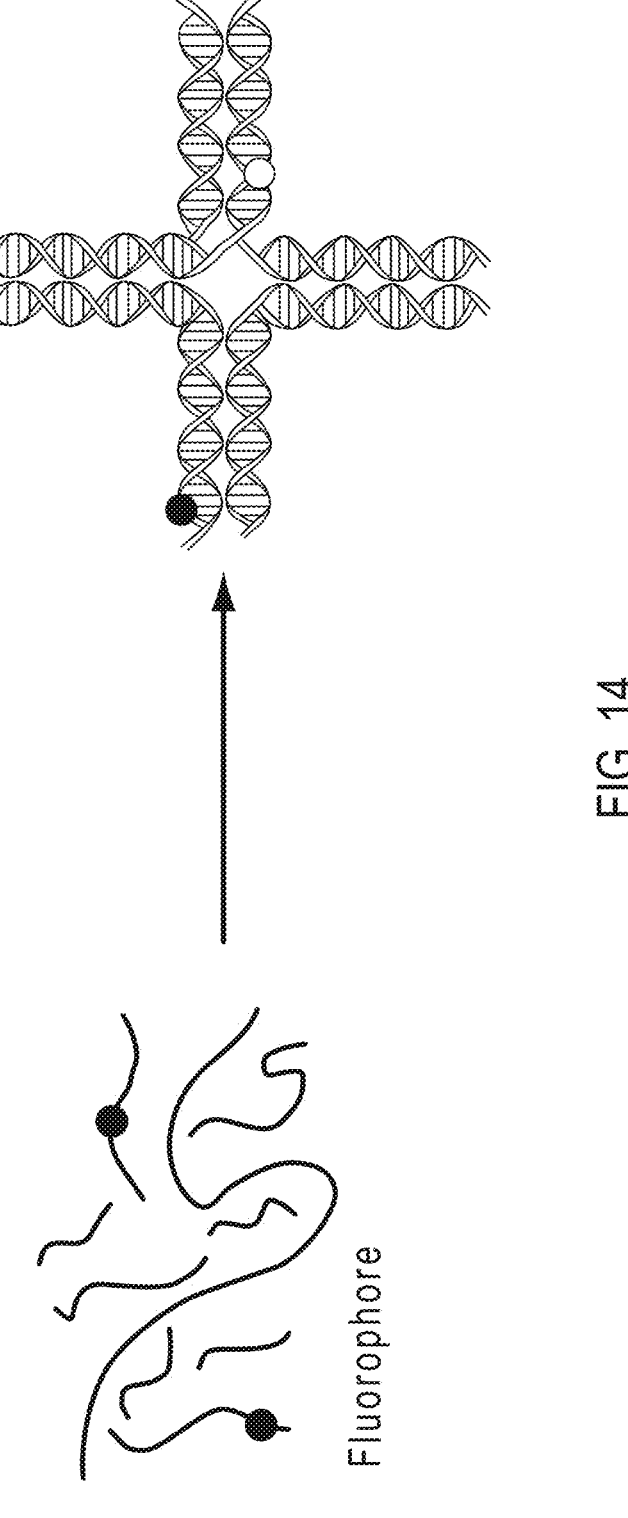
FIG. 14 shows self-assembly of fluorophore-functionalized single-stranded DNA (ssDNA) into a folded oligonucleotide-based fluorescent label structure of this disclosure.

Oligonucleotide-based fluorescent labels have been described in detail in WO/2018/231805, which is incorporated herein by reference in its entirety. Oligonucleotide-based fluorescent labels which can be used as labels can be created via a variety of techniques. In some examples, DNA self-assembly can be used to ensure that the relative locations of the resonators within a label correspond to locations specified according to a desired temporal decay profile. For example, each resonator of the network could be coupled to a respective specified DNA strand (FIG. 14). Each DNA strand could include one or more portions that complement portions one or more other DNA strands such that the DNA strands self-assemble into a nanostructure that maintains the resonators at the specified relative locations.

DNA self-assembly and other emerging nano-scale manufacturing techniques permit the fabrication of many instances of a specified structure with precision at the nano-scale. For example, as described in WO/2018/231805, a PHITON is made by annealing custom, synthetic DNA produced by chemical methods. The multiple strands are pre-conjugated to fluorophores, peptides, small molecules, etc. prior to being mixed and annealed. The sequences are designed such that there is a single, finite assembly of lowest energy and is stable in solution, dry, or frozen and preserves the relative location of any conjugated materials. Such precision can permit fluorophores, quantum dots, dye molecules, plasmonic nanorods, or other optical resonators to be positioned at precise locations and/or orientations relative to each other in order to create a variety of optical resonator networks. Such resonator networks may be specified to facilitate a variety of different applications. In some examples, the resonator networks could be designed such that they exhibit a pre-specified temporal relationship between optical excitation (e.g., by a pulse of illumination) and re-emission; this could enable temporally-multiplexed labels and taggants that could be detected using a single excitation wavelength and a single detection wavelength. Additionally or alternatively, the probabilistic nature of the timing of optical re-emission, relative to excitation, by these resonator networks could be leveraged to generate samples of a random variable. These resonator networks may include one or more "input resonators" that exhibit a dark state; resonator networks including such input resonators may be configured to implement logic gates or other structures to control the flow of excitons or other energy through the resonator network. Such structures could then be used, e.g., to permit the detection of a variety of different analytes by a single resonator network, to control a distribution of a random variable generated using the resonator network, to further multiplex a set of labels used to image a biological sample, or to facilitate some other application.

These resonator networks include networks of fluorophores, quantum dots, dyes, Raman dyes, conductive nanorods, chromophores, or other optical resonator structures. The networks can additionally include antibodies, aptamers, strands of deoxyribonucleic acid (DNA) or ribonucleic acid (RNA), or other receptors configured to permit selective binding to analytes of interest (e.g., to a surface protein, molecular epitope, characteristic nucleotide sequence, or other characteristic feature of an analyte of interest). The labels can be used to observe a sample, to identify contents of the sample (e.g., to identity cells, proteins, or other particles or substances within the sample), to sort such contents based on their identification (e.g., to sort cells within a flow cytometer according to identified cell type or other properties), or to facilitate some other applications. In certain embodiments disclosed herein the labels a linked to a substrate, such as an antibody or bead, via a polynucleotide linker.

In an example application, such resonator networks may be applied (e.g., by-coupling the resonator network to an antibody, aptamer, or other analyte-specific receptor) to detect the presence of, discriminate between, or otherwise observe a large number of different labels in a biological or material sample or other environment of interest. Such labels may permit detection of the presence, amount, or location of one or more analytes of interest in a sample (e.g., in a channel of a flow cytometry apparatus). Having access to a large library of distinguishable labels can allow for the simultaneous detection of a large number of different analytes. Additionally or alternatively, access to a large library of distinguishable labels can allow for more accurate detection of a particular analyte (e.g., a cell type or sub-type of interest) by using multiple labels to bind with the same analyte, e.g., to different epitopes, surface proteins, or other features of the analyte. Yet further, access to such a large library of labels may permit selection of labels according to the probable density or number of corresponding analytes of interest, e.g., to ensure that the effective brightness of different labels, corresponding to analytes having different concentrations in a sample, is approximately the same when optically interrogating such a sample.

Such labels may be distinguishable by virtue of differing with respect to an excitation spectrum, an emission spectrum, a fluorescence lifetime, a fluorescence intensity, a susceptibility to photobleaching, a fluorescence dependence on binding to an analyte or on some other environmental factor, a polarization of re-emitted light, or some other optical properties. However, it can be difficult to produce a large library of distinguishable labels when relying on differences with respect to emission or excitation spectrum due to limitations on the available fluorophores or other optical distinguishable substances and limitations on the wavelength transparency/compatibility of common sample materials of interest.

WO/2018/231805 describes methods for specifying, fabricating, detecting, and identifying optical labels that differ with respect to temporal decay profile and/or excitation and emission spectra. Additionally or alternatively, the provided labels may have enhanced brightness relative to existing labels (e.g., fluorophore-based labels) and may have a configurable brightness to facilitate panel design or to permit the relative brightness of different labels to facilitate some other consideration. Such labels can differ with respect to the time-dependent probability of re-emission of light by the label subsequent to excitation of the label (e.g., by an ultra-fast laser pulse). Additionally or alternatively, such labels can include networks of resonators to increase a difference between the excitation wavelength of the labels and the emission wavelength of the labels (e.g., by interposing a number of mediating resonators between an input resonator and an output resonator to permit excitons to be transmitted between input resonators and output resonators between which direct energy-transfer is disfavored). Yet further, such labels may include logic gates or other optically-controllable structures to permit further multiplexing when detecting and identifying the labels.

Resonator networks (e.g., resonator networks included as part of labels) as described in WO/2018/231805 can be fabricated in a variety of ways such that one or more input and/or readout resonators, output resonators, dark-state-exhibiting "logical input" resonators, and/or mediating resonators are arranged according to a specified network of resonators and further such that a temporal decay profile of the network, a brightness of the network, an excitation spectrum, an emission spectrum, a Stokes shift, or some other optical property of the network, or some other detectable property of interest of the network (e.g., a state of binding to an analyte of interest) corresponds to a specification thereof (e.g., to a specified temporal decay profile, a probability of emission in response to illumination). Such arrangement can include ensuring that a relative location, distance, orientation, or other relationship between the resonators (e.g., between pairs of the resonators) correspond to a specified location, distance, orientation, or other relationship between the resonators.

This can include using DNA self-assembly to fabricate a plurality of instances of one or more resonator networks. For example, a number of different DNA strands could be coupled (e.g., via a primary amino modifier group on thymidine to attach an N-Hydroxysuccinimide (NHS) ester-modified dye molecule) to respective resonators of a resonator networks (e.g., input resonators, output resonator, and/or mediator resonators). Pairs of the DNA strands could have portions that are at least partially complementary such that, when the DNA strands are mixed and exposed to specified conditions (e.g., a specified pH, or a specified temperature profile), the complementary portions of the DNA strands align and bind together to form a semi-rigid nanostructure that maintains the relative locations and/or orientations of the resonators of the resonator networks.

Figure 15:
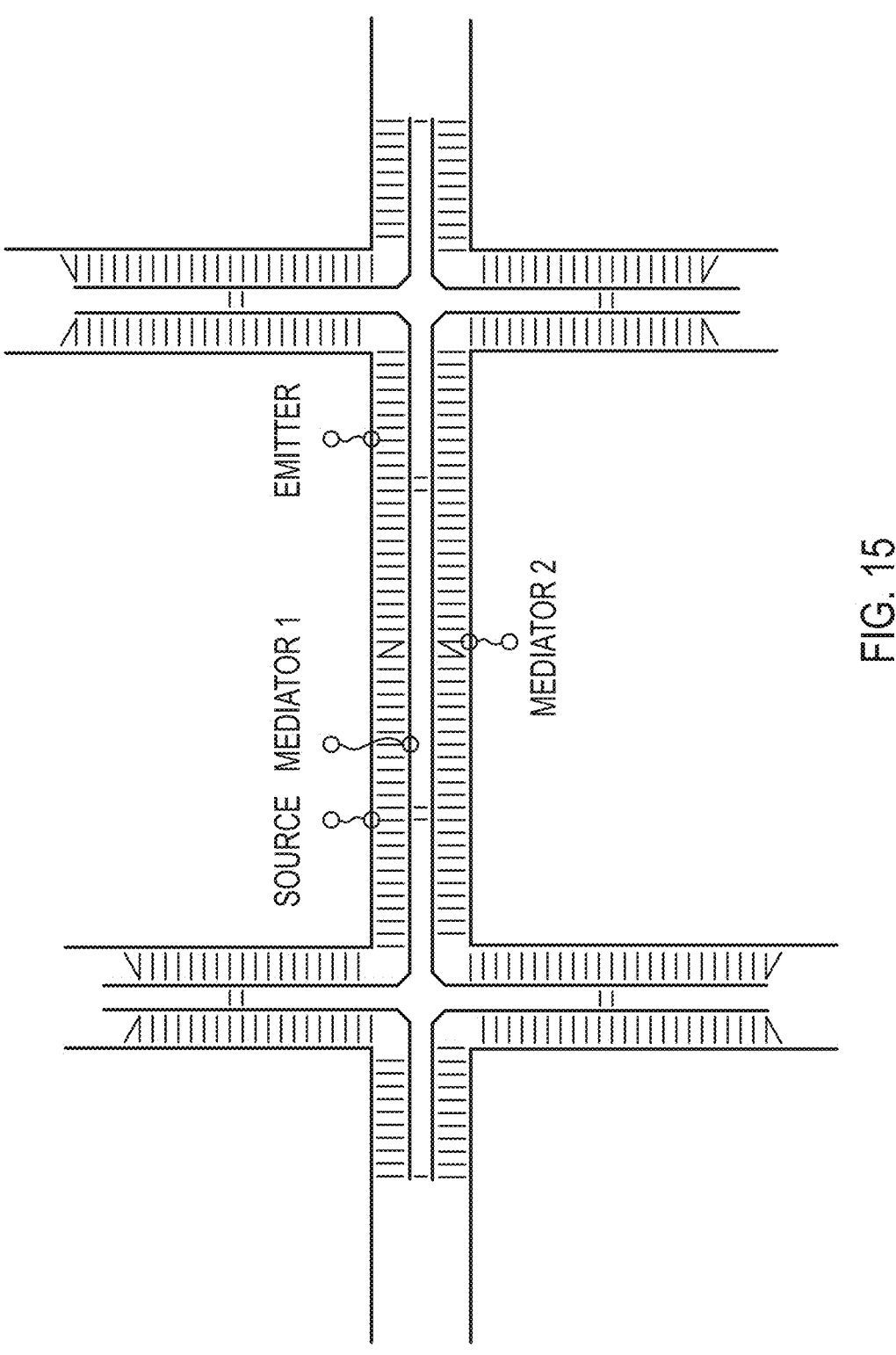
FIG. 15 shows a schematic of resonator networks coupled to DNA strands to form an oligonucleotide-based fluorescent label.
Figure 16:
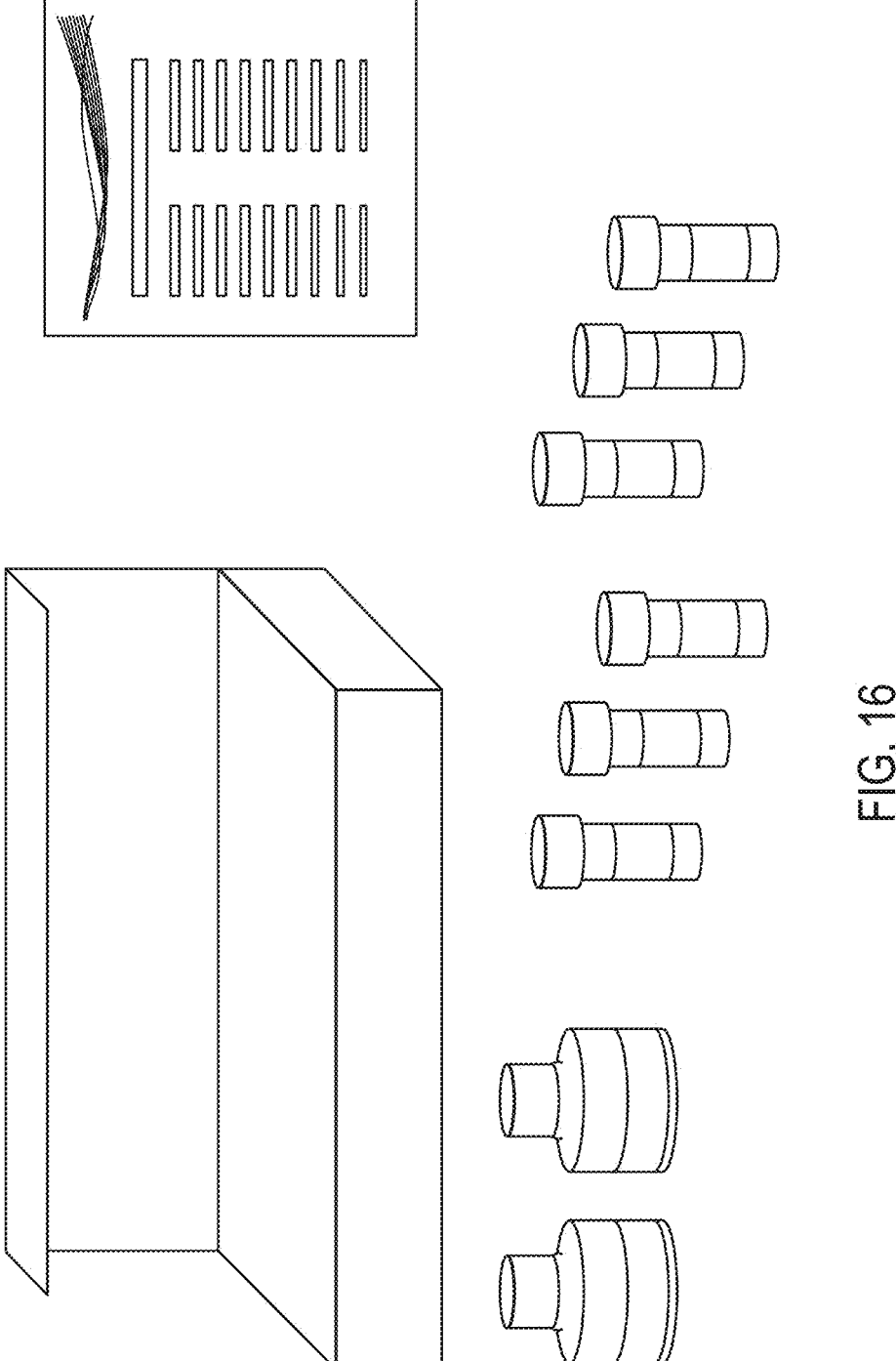
FIG. 16 shows a schematic of a kit used to conjugate labels to substrates such as beads or antibodies or derivatives.

FIG. 15 shows a schematic of such a resonator network. An input resonator, an output resonator and two mediator resonators are coupled to respective DNA strands. The coupled DNA strands, along with additional DNA strands, then self-assemble into the illustrated nanostructure such that the input resonator, mediator resonators, and output resonator form a resonator wire. In some examples, a plurality of separate identical or different networks could be formed, via such methods or other techniques, as part of a single instance of a resonator network (e.g., to increase a brightness of the resonator network).

The distance between resonators of such a resonator network could be specified such that the resonator network exhibits one or more desired behaviors (e.g., is excited by light at a particular excitation wavelength and responsively re-emits light at an emission wavelength according to a specified temporal decay profile). This can include specifying the distances between neighboring resonators such that they are able to transmit energy between each other (e.g., bidirectionally or unidirectionally) and further such that the resonators do not quench each other or otherwise interfere with the optical properties of each other. In examples wherein the resonators are bound to a backbone via linkers (e.g., to a DNA backbone via an amide bond (created, e.g., by N-Hydroxysuccinimide (NHS) ester molecules) or other linking structures), the linkers can be coupled to locations on the background that are specified with these considerations, as well as the length(s) of the linkers, in mind. For example, the coupling locations could be separated by a distance that is more than twice the linker length (e.g., to prevent the resonators from coming into contact with each other, and thus quenching each other or otherwise interfering with the optical properties of each other). Additionally or alternatively, the coupling locations could be separated by a distance that is less than a maximum distance over which the resonators may transmit energy between each other. For example, the resonators could be fluorophores or some other optical resonator that is characterized by a Forster radius when transmitting energy via Forster resonance energy transfer, and the coupling locations could be separated by a distance that is less than the Forster radius.

Example Systems and Methods for Identifying Labels in a Sample.

It can be beneficial in a variety of applications to interrogate a sample (e.g., a biological sample, or a stream of cells in a flow cytometer) or some other environment of interest in order to detect the presence, identity, absolute or relative amount, or other properties of labels as described herein that may be present in the sample or other environment of interest. Such interrogation could facilitate imaging of a sample, e.g., to determine the location, concentration, or other information about one or more analytes that are present within the sample and to which one or more varieties of labels are configured to bind. Such interrogation could facilitate the identification of cells, proteins, strands of RNA, or other contents of a sample in order to sort such contents or to provide some other benefit. For example, a flow cytometry apparatus could include a flow channel through which cells (or other particles of interest) flow. Such a flow channel could be interrogated as described herein in order to identify one or more labels in the channel and/or to identify the type or subtype of the cells, to determine a property of the cells, or to determine some other information based on the identified labels. Such information could then be used to sort the cells, e.g., according to cell type.

Such methods for detecting and/or identifying labels in an environment of interest could include providing illumination to the environment of interest (e.g., in the form of one or more ultrashort pulses of illumination) and detecting one or more properties of photons emitted from the environment in response to the illumination (e.g., a wavelength or spectrum of such photons, a timing of emission of such photons relative to a timing of the illumination, e.g., of one or more pulses of the illumination). This could include providing a single pulse of illumination and detecting the photons responsively emitted from a plurality of instances of one or more labels in the environment. Additionally or alternatively, one or more instances of one or more labels could be illumination a plurality of times by a plurality of pulses of illumination and the timing, relative to the pulses of illumination, of responsively emitted photons could be detected. Information about the timing of the responsively emitted photons could then be used to identify one or more labels that are present in the environment, to determine a binding state or other properties of such labels, to determine absolute or relative amounts of the label(s) in the environment, or to determine some other information related to one or more labels as described herein that are present in the environment.

Illumination could be provided to an environment as one or more pulses of illumination. The provided illumination could have a specified wavelength, e.g., an excitation wavelength of an input resonator of one or more of the labels. Such an excitation wavelength could be common across some or all of the labels present in the environment of interest, e.g., due to some or all of the labels including the same fluorophore, quantum dot, dye, or other optical substance or structure as their input resonator(s). Additionally or alternatively, multiple different wavelengths of light could be provided to excite multiple different input resonators, e.g., of multiple different labels. In some examples, such different wavelengths of light could be provided at different points in time (e.g., as part of different pulses of illumination) to facilitate spectrally-multiplexed detection of multiple different labels and/or multiple different sets of labels. In some examples, a single label could include multiple different input resonators, and the different input resonators could be excited by light at respective different wavelengths, e.g., as part of respective different pulses of illumination.

In order to improve the identification of labels in an environment, pulses of illumination used to interrogate the environment could be ultrashort pulses (e.g., pulses having durations on the order of attoseconds to nanoseconds). Such ultrashort pulses could be provided as broadband pulses emitted from a mode-locked oscillator. In examples wherein a label includes resonators having long-lifetime states (e.g., lanthanide atoms or other lanthanide compounds or complexes), the pulses of illumination could have longer durations, e.g., on the order of microseconds.

The timing, relative to such a pulse of illumination, of emission of photons from the environment in response to the pulse of illumination could be detected in a variety of ways. In some examples, the timing of individual photons could be detected, e.g., using one or more single-photon avalanche diodes, photomultipliers, or other single-photon detectors. The outputs of such detectors could be used, as part of a time-correlated single photon counter, to determine a count of photons determined as a function of time after a pulse of illumination is provided to the environment. The timing of such detected photons could be used to determine a probability density function for the timing of emission of photons from the sample in response to illumination of the sample.

Additionally or alternatively, detecting the timing of emission of photons from the environment could include detecting a timing of one or more peaks in the rate or intensity of the emitted photons, or detecting some other aggregate property of the timing of the emitting photons (e.g., to determine a delay timing of a peak of the rate of emission of photons that could be matched to the delay of a corresponding peak of a known temporal decay profile). Such detection could include applying a peak detector, a differentiator, a matched filter, or some other analog or digital signal processing techniques to the output of a single-photon avalanche diode or other photodetector element that is configured to receive photons emitted from the environment of interest.

One or more known labels could be present in an environment of interest and it could be beneficial to determine the identity of such labels and/or to determine some other information about the labels in the environment. As described above, such labels could be distinguished according to their temporal decay profiles; that is, each known label could be characterized by a respective different temporal decay profile. Thus, the identity of the one or more labels present in the environment could be determined by comparing the detected timing of emission of photons from the environment to a dictionary of temporal decay profiles, where each of the temporal decay profiles in the dictionary corresponds to a respective known label that could be present in the environment.

Interrogating an environment could include detecting the timing of emission of photons within multiple different ranges of wavelengths. This could be done to detect the timing of emission of photons from two different output resonators of a label. Additionally or alternatively, this could be done to detect the timing of emission of photons from an output resonator, one or more mediating resonators, and/or an input resonator of the label.

Yet further, one or more of the labels present in the environment may include dark-state-exhibiting resonators such that the temporal decay profile of the labels is dependent on whether the dark-state-exhibiting resonators are in their respective dark states. For example, a label could include a first dark-state-exhibiting resonator and could exhibit a first temporal decay profile when the first dark-state-exhibiting resonator is in its dark state and the label could exhibit a second temporal decay profile when the first dark-state-exhibiting resonator is not in its dark state. In such examples, detection and/or identification of the label could include detecting a timing of optical excitation and re-emission during a time period when the dark-state-exhibiting resonator(s) is not in its dark state and, during a different period of time, inducing the dark-state-exhibiting resonator(s) to enter the dark state (e.g., by providing illumination at an excitation wavelength of the dark-state-exhibiting resonator(s)) and again detecting a timing of optical excitation and re-emission of the label.

EXAMPLES

Example 1

Figure 11:
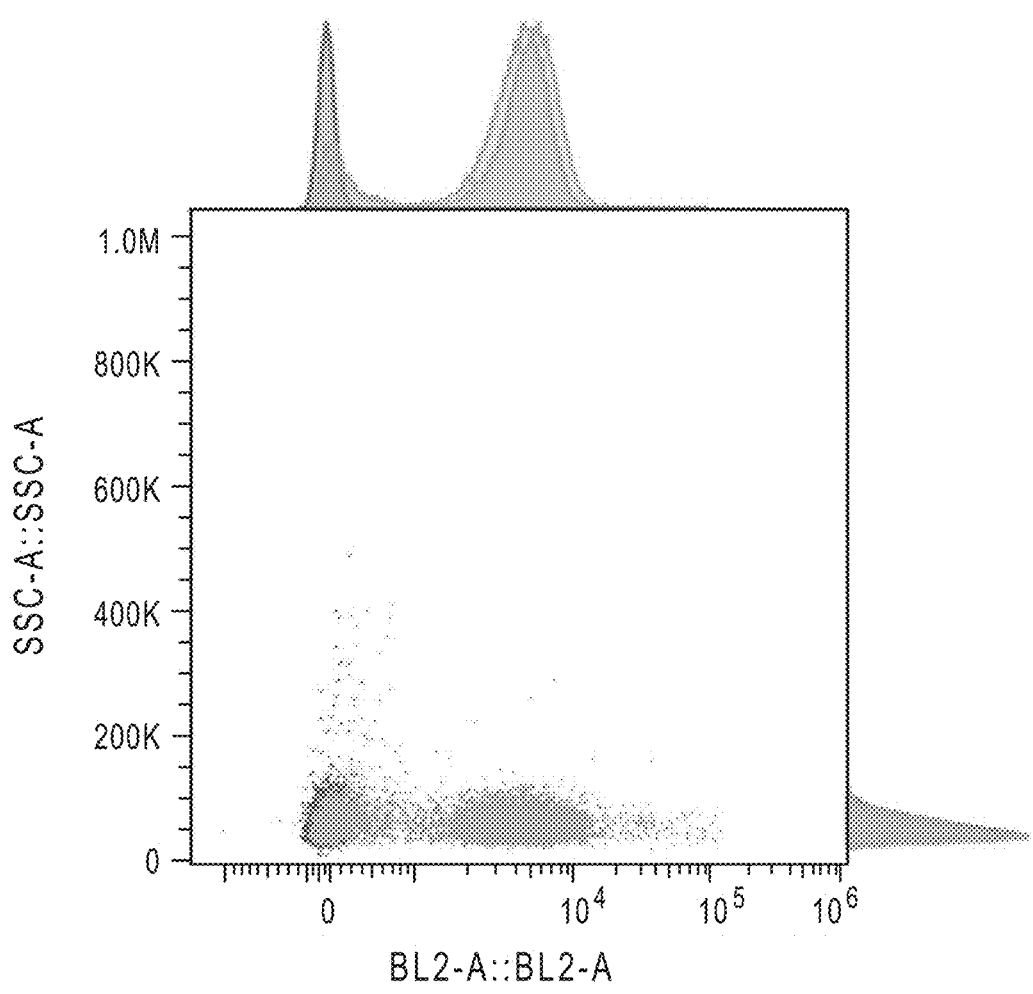
FIG. 11 shows a performance comparison (staining peripheral blood mononuclear cells, PBMCs) of PHITON Label (NovaBlue 610) conjugated to an anti-CD3 antibody using the method described herein (polyT) versus conjugation to a unique identifying "barcode" sequence.
Figure 12:
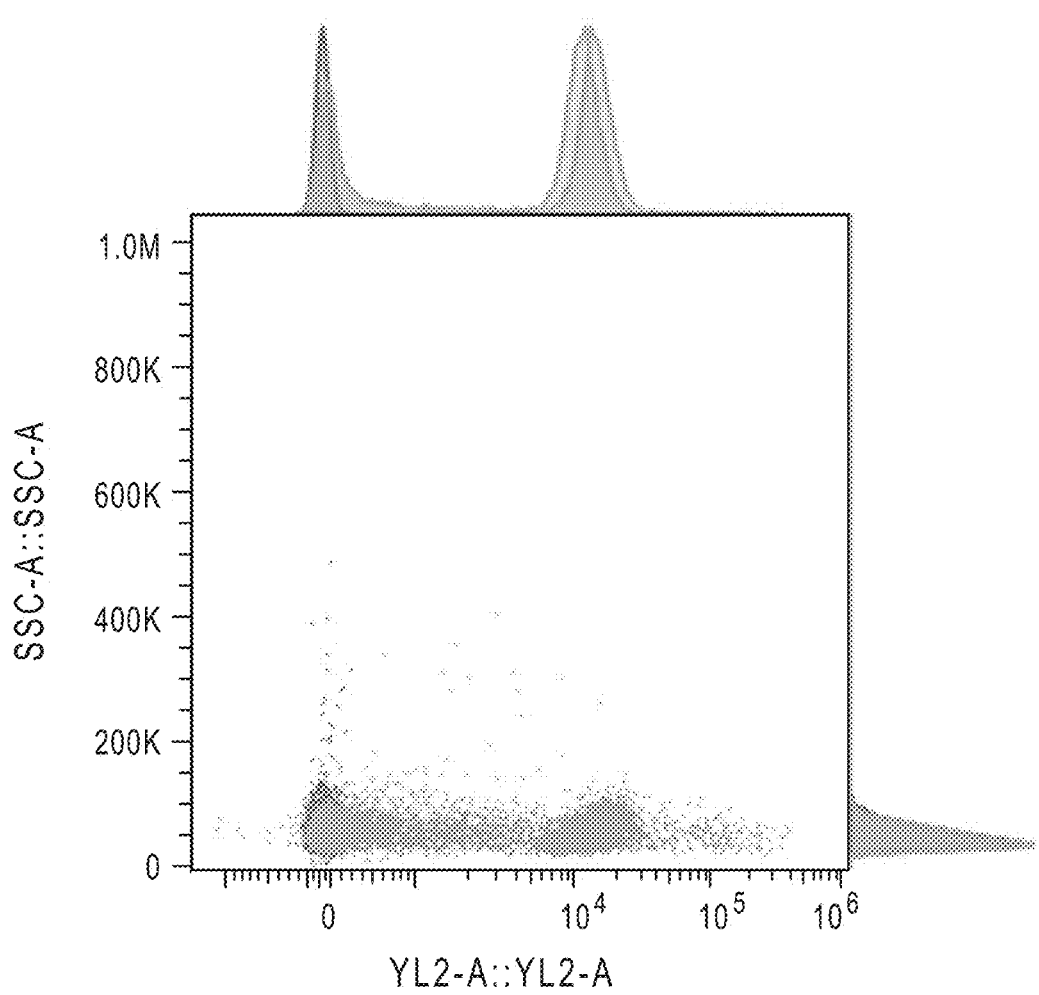
FIG. 12 shows a performance comparison (staining peripheral blood mononuclear cells, PBMCs) of PHITON Label (NovaYellow 610) conjugated to an anti-CD4 antibody using the method described herein (polyT) versus conjugation to a unique identifying "barcode" sequence.

It is important to note that the use of a polynucleotide sequence rather than a unique, highly varied sequence can significantly impact conjugation yields and/or performance of the conjugate in downstream applications. FIG. 11 and FIG. 12 illustrate this using Peripheral blood mononuclear cell (PBMC) staining data comparing the performance of PHITON-labeled antibodies conjugated using both highly varied sequences as well as polynucleotide sequences. The overlay of these two datasets shows that both conjugation methods produce nearly identical staining patterns and thus do not significantly alter the conjugation yield or the staining results.

Example 2

Figure 13:
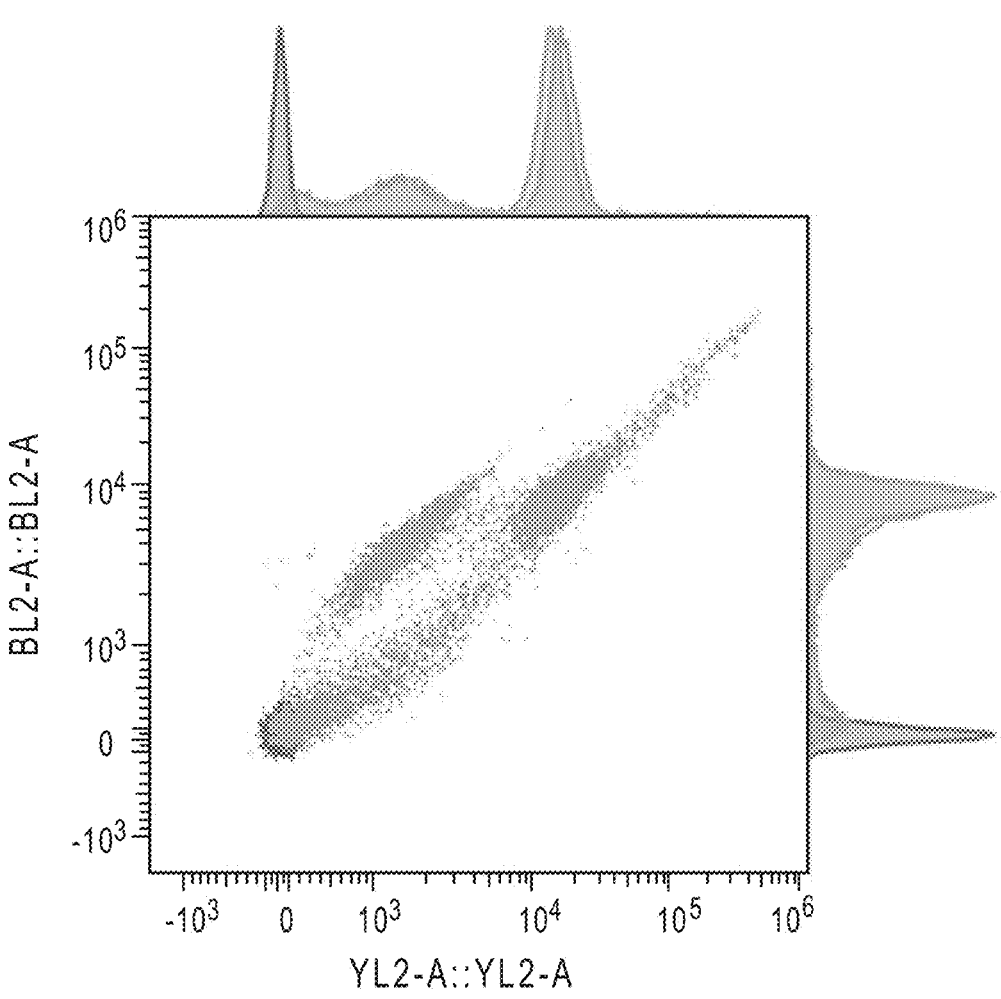
FIG. 13 shows a performance comparison (staining peripheral blood mononuclear cells, PBMCs) with PHITON labels (NovaBlue 610 and Nova Yellow 610) which have been conjugated to anti-CD3 and anti-CD4 respectively antibody using the method described herein (polyT) versus the same dyes conjugated via a unique identifying "barcode" sequence.

Conjugates using the same polynucleotide sequences can also be mixed together post-conjugation and remain stable in solution without exhibiting significant exchange, i.e., denaturation of one conjugate and re-hybridization of the byproducts with other species in the mixture. FIG. 13 illustrates this with PBMCs that have been stained with a mixture of Nova-Blue 610-CD3 and Nova Yellow 610-CD4 using both highly varied and unique sequences, and the same polynucleotide sequences for both conjugates. The overlay in FIG. 13 shows that results are nearly identical regardless of whether unique sequences are used or the same polynucleotide sequence.

Example 3

Beads comprising one or more (generally a plurality) single-stranded nucleic acid linkers (e.g., polyA) attached can be used to purify unconjugated polynucleotide-modified dyes after annealing with polynucleotide-modified antibodies using the affinity of their unbound linkers (e.g. polyT) to bind to the surface of the bead. FIG. 10 illustrates this process wherein a mixture of bound and unbound dye are reacted with polyA beads, washed, and centrifuged (removed) to yield a purified supernatant.

Such purification produces a waste product (e.g., removed, unbound dye), that can be recycled by displacing the linkage between the dye and the polyA bead using a longer free polyT strand of 10-20 nucleotides wherein the dye linkage is not to the entire polyA strand but less by 1-10 nucleotides. This process will exchange the dye for the free polyT strand and after washing and centrifugation, will leave purified, unbound dye in the supernatant suitable for re-conjugation to an antibody.

Example 4

The brightness of a conjugate can be increased while retaining the optical properties by changing the stoichiometry. For example, if the dye:protein (D:P) ratio is changed to 2 for a 2-core dye, this would give a 4 fold amplification of the brightness of a given dye. As another example, with a D:P ratio of 4 and a fully loaded single dye label (for example, 16 individual dyes on a PHITON), we could get to $4 \times 16 = 64 \times$ brightness which would bring a (still quantitative) way to detect a very, very low (and currently undetectable) number of molecules on an individual cell.

Example 5

Figures 19A, 19B, 19C:
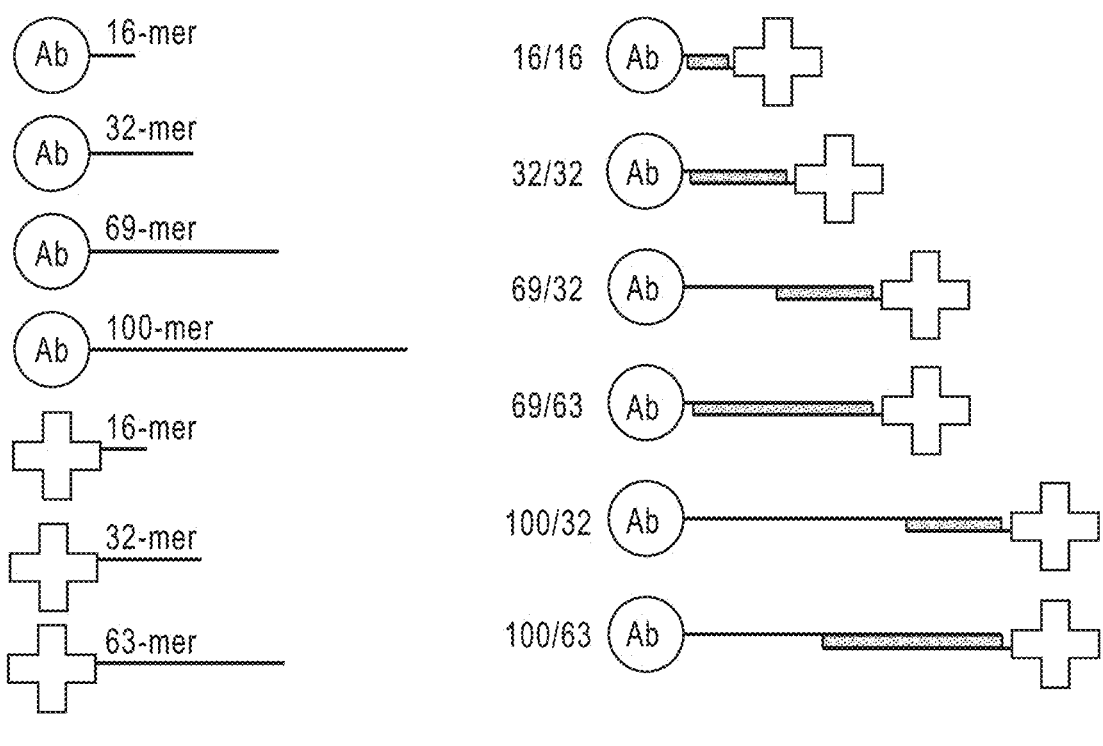
FIG. 19A shows antibodies and fluorescent polynucleotide-modified conjugate components (e.g., oligonucleotide-based fluorescent labels, PHITONs, and the like) that were modified with varying lengths of ssDNA linkers that completely or partially hybridized to one another.
FIG. 19B shows the various antibody-polynucleotide-modified conjugate component conjugates using different combinations of the individual components shown in FIG. 19A.
FIG. 19C shows a polyacrylamide gel electrophoresis (PAGE) gel showing antibody-ssDNA linker conjugates for each of the four lengths of ssDNA linker on the antibody (16, 32, 69, 100 nucleotides) after purification to remove unmodified antibody.

An optimized method for modifying antibodies with single-stranded DNA (ssDNA) can be used to attach oligos of varying lengths. This method entails optimized chemistry to control the degree of labeling of the ssDNA linker, as well as purification methods to remove excess ssDNA linker and unlabeled antibody. FIG. 19A through FIG. 21B show data obtained exploring four different lengths of ssDNA linker attached to anti-human CD4 antibody (clone SK3). A complementary ssDNA linker sequence was incorporated into a fluorescent polynucleotide-modified conjugate component (e.g., a PHITON or oligonucleotide-based fluorescent label) during folding that could hybridize to all or a portion of the ssDNA linker sequence on the antibody. FIG. 19B shows how a small subset of linker lengths on the antibody and the fluorescent polynucleotide-modified conjugate component were combined in different ways to give six different antibody-fluorescent polynucleotide-modified conjugate component conjugates with varying lengths of double- and single-stranded linkage. FIG. 19C shows a PAGE gel of the antibody conjugates with varying lengths of nucleic acid linker after purification. When tested in flow cytometry (FIGS. 20A-20D) using conjugates of anti-human CD4 antibody (clone SK3) and NOVAFLUOR Yellow 610 (the fluorescent polynucleotide-modified conjugate component) to stain human peripheral blood mononuclear cells (PBMCs), the varying combinations of linkers influenced the brightness of the signal detected. Such a method illustrated how fluorescent polynucleotide-modified conjugate components can be used to explore the effects of length and sequence on epitope binding for the fluorescent polynucleotide-modified antibody conjugate.

FIG. 19A shows antibodies and fluorescent polynucleotide-modified conjugate components (e.g., PHITONs or oligonucleotide-based fluorescent labels) that were modified with varying lengths of ssDNA linkers that completely or partially hybridized to one another. FIG. 19B shows the various conjugates of antibody and fluorescent polynucleotide-modified conjugate components using different combinations of the individual components shown in FIG. 19A. FIG. 19C shows a polyacrylamide gel electrophoresis (PAGE) gel showing antibody-ssDNA linker conjugates for each of the four lengths of ssDNA linker on the antibody (16, 32, 69, 100 nucleotides) after purification to remove unmodified antibody.

Figures 20A, 20B:
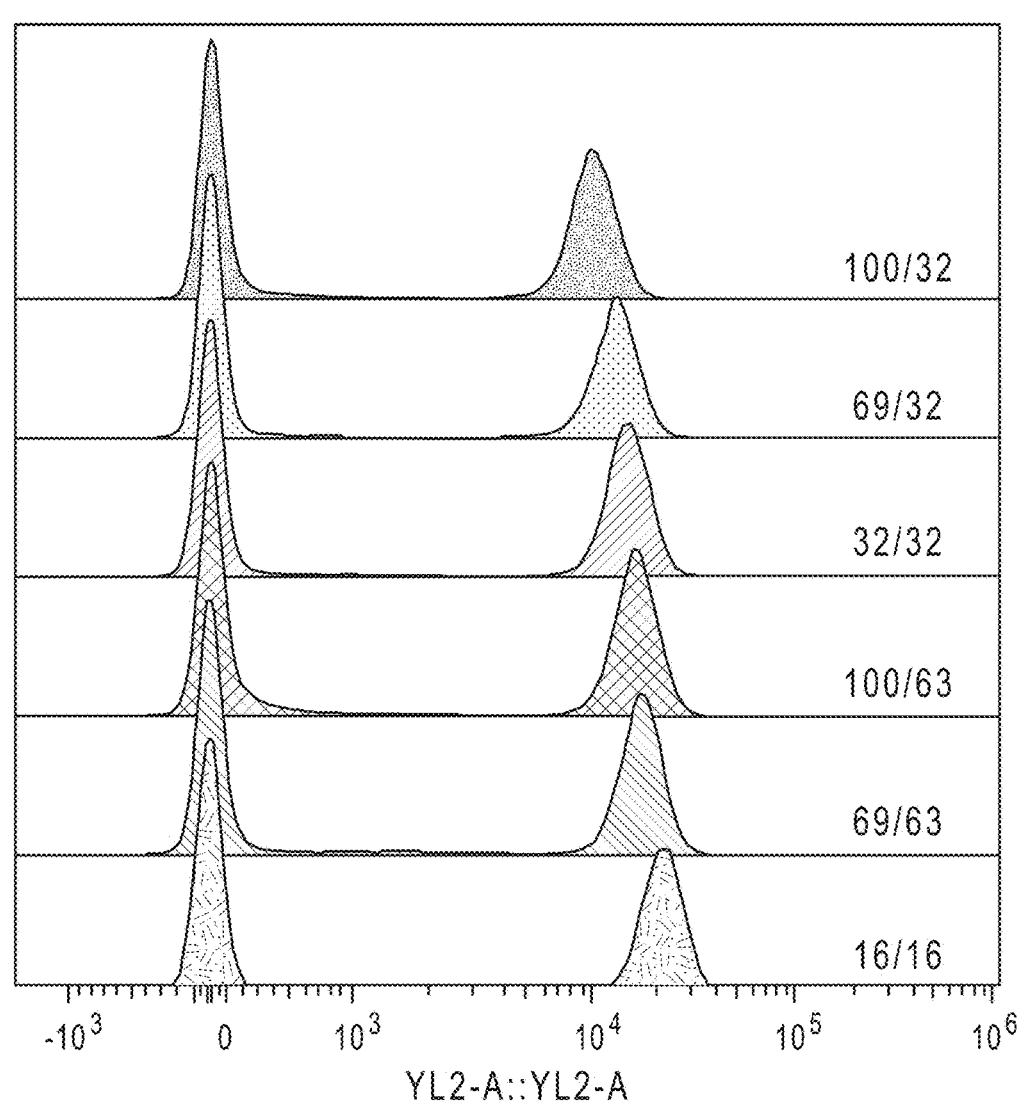
FIG. 20A shows flow cytometry data from human PBMCs testing the various possible combinations of nucleic acid linkers for attaching a fluorescent polynucleotide-modified conjugate component (in this example NOVAFLUOR Yellow 610) to anti-Human CD4 antibody (clone SK3). All conjugates were compared at the same dose.
FIGS. 20B and 20C show analysis of the flow cytometry data comparing the median fluorescence intensity (MFI) of the CD4+ population and the separation indices (SI) of the various antibody-NOVAFLUOR Yellow 610 conjugates. The composition of the nucleic acid linker strongly influenced the performance of the conjugate in flow cytometry.
Figure 20C:
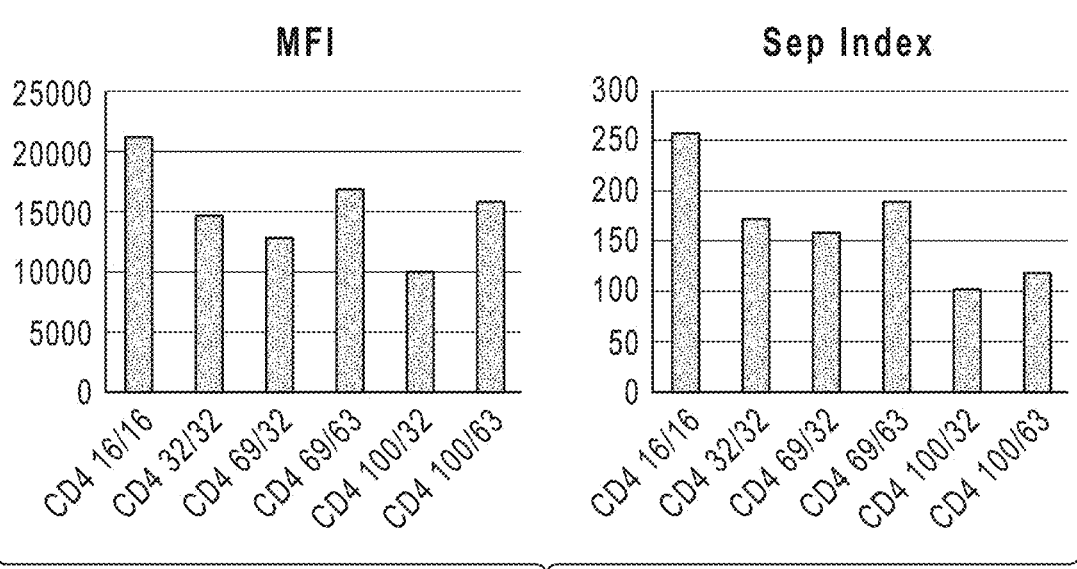
Figure 20D:
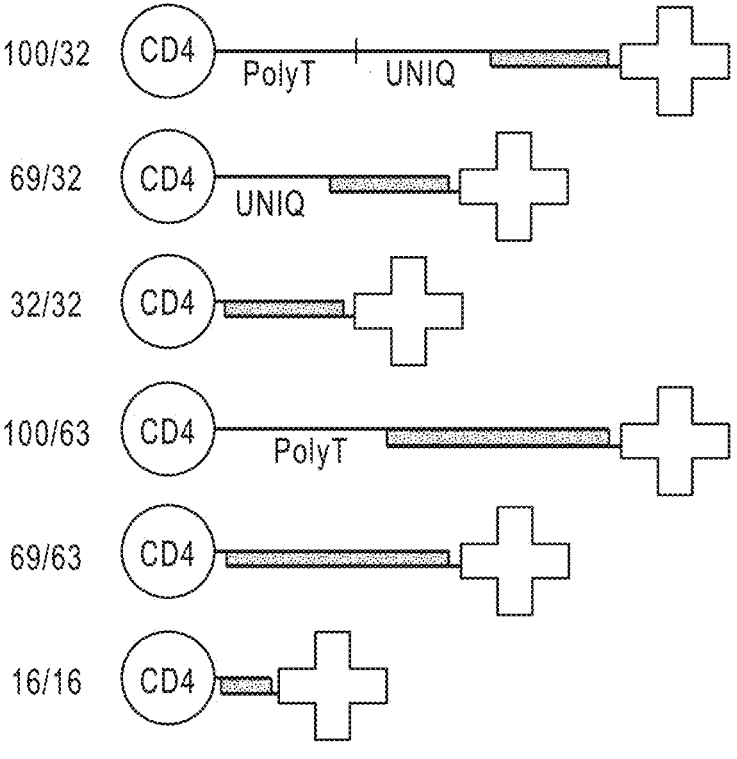
FIG. 20D shows the composition of the nucleic acid linkers for each of the conjugates, specifically whether the linker was partially or fully double-stranded and whether the single-stranded portion of the nucleic acid linker contained a poly(T) region and/or a unique identifying sequence (UNIQ).

FIG. 20A shows flow cytometry data from human PBMCs testing the various possible combinations of linkers for attaching a fluorescent polynucleotide-modified conjugate component (in this example NOVAFLUOR Yellow 610) to anti-Human CD4 (SK3) antibody. All conjugates were compared at the same dose. FIGS. 20B and 20C show analysis of the flow cytometry data that compared the median fluorescence intensity (MFI) of the CD4+ population and the separation indices (SI) of the various antibody-NOVAFLUOR Yellow 610 conjugates. The composition of the nucleic acid linker strongly influenced the performance of the conjugate in flow cytometry. FIG. 20D shows the composition of the nucleic acid linkers for each of the conjugates, specifically whether the linker was partially or fully double-stranded and whether the single-stranded portion of the nucleic acid linker contained a poly(T) region and/or a unique identifying sequence (UNIQ).

The effect of the nucleic acid linker composition and length of the double-stranded portion was investigated in FIG. 19A through FIG. 21B. A variety of antibody-fluorescent polynucleotide-modified conjugate component conjugates were made and are depicted in FIG. 19B. Some of the conjugates had a short, fully double-stranded linker as seen in FIG. 19B, conjugates 16/16 and 32/32, whereas others had a longer nucleic acid linker that was partially double-stranded as seen in FIG. 19B, conjugates 69/32, 69/63, 100/32 and 100/63. As shown in FIGS. 20A-20D, the composition of the nucleic acid linker strongly influenced the median fluorescence intensity (MFI) of the conjugates as well as the performance of the conjugates in flow cytometry.

Figure 21A:
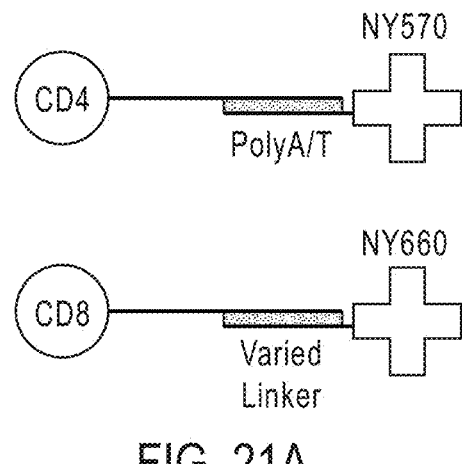
FIG. 21A shows anti-human CD4 antibody (clone SK3) conjugated to NOVAFLUOR Yellow 570 and anti-human CD8 antibody (clone OKT-8) conjugated to NOVAFLUOR Yellow 660 using two different nucleic acid linker sequences (Poly(A)/Poly(T) for the CD4 conjugate and a more varied sequence "varied linker" for the CD8 conjugate).
Figure 21B:
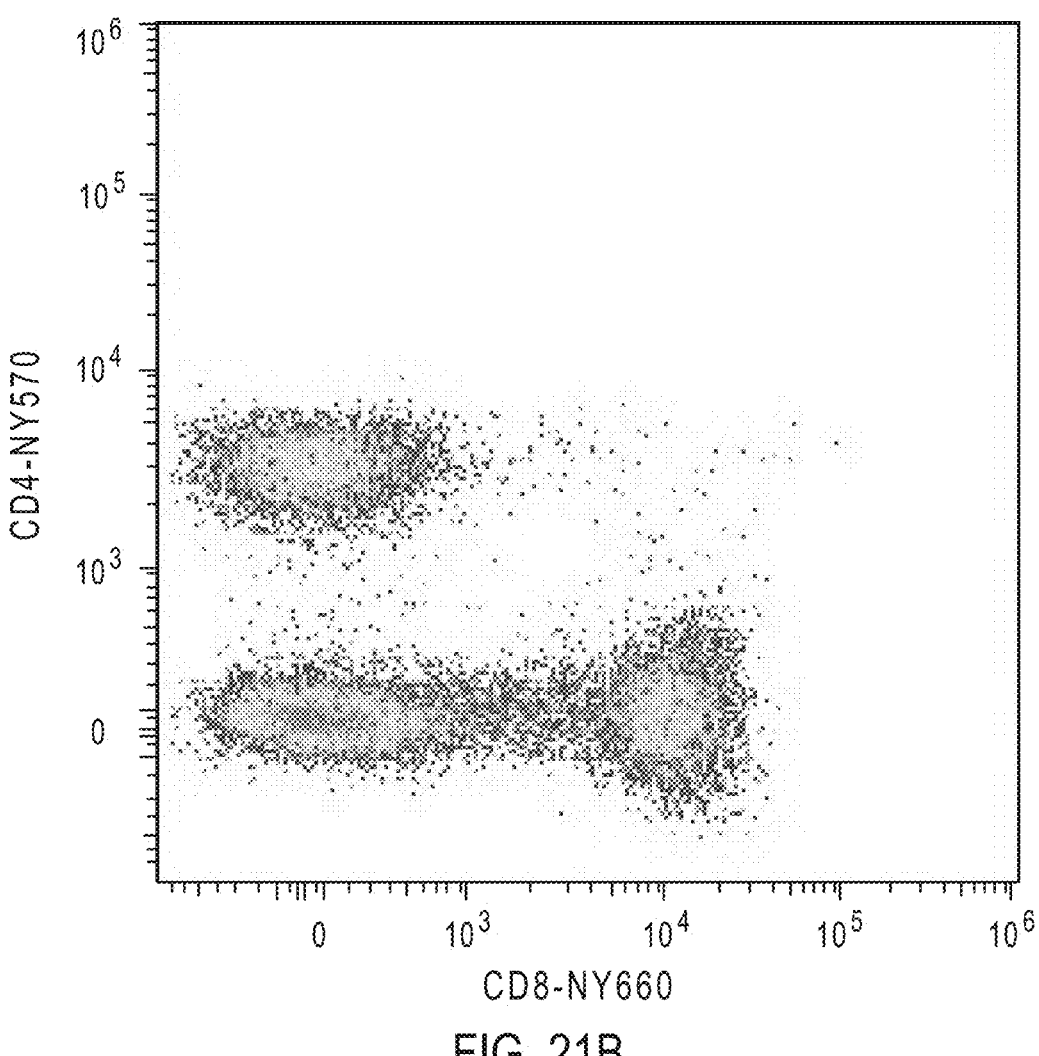
FIG. 21B shows flow cytometry data showing co-staining of the CD4 and CD8 conjugates described in FIG. 21A on PBMCs.

Surprisingly, it was found that the shorter nucleic acid linkers that were fully double-stranded had the best performance, see FIGS. 20A-20D, conjugates 16/16 and 69/63. Intermediate performance was seen with the 32-mer or the partially double-stranded nucleic acid linker with an exposed poly(T) region, see FIGS. 20A-20D, conjugates 32/32 and 100/63. The poorest performance was observed with partially double-stranded nucleic acid linkers with an exposed unique identifying sequence, see FIGS. 20A-20D, conjugates 69/32 and 100/32. Separately, DNA linkers with distinct sequences were tested with different antibody-fluorescent polynucleotide-modified conjugate component conjugates to illustrate that more than one of these reagents can be used together in the same multiplexed experiment. FIGS. 21A-21B show anti-human CD4 antibody (clone SK3) conjugated to NOVAFLUOR Yellow 570 and anti-human CD8 antibody (clone OKT-8) conjugated to NOVAFLUOR Yellow 660 assembled with a poly(A)/poly(T) linker (CD4 conjugate) and a more varied nucleic acid linker sequence (CD8 conjugate). These conjugates were used together to distinctly stain their target populations on human PBMCs with no cross-reactivity. Such a strategy could be extended to other unique DNA sequences and illustrates the feasibility of using many of these conjugates together in the workflows discussed.

The breadth and scope of the present disclosure should not be limited by any of the above-described exemplary embodiments, but should be defined only in accordance with the following claims and their equivalents.

What is claimed is:

1. A fluorescently labeled bioconjugate comprising:

a substrate comprising a binding molecule linked to an oligonucleotide-based fluorescent label via a partially double-stranded nucleic acid linker that has a length of from 60 to 75 nucleotides;

wherein the substrate comprises a first single-stranded nucleic acid linker and the oligonucleotide-based fluorescent label comprises a second single-stranded nucleic acid linker, wherein the first and second single-stranded nucleic acid linkers are fully single-stranded;

wherein a portion of the first single-stranded nucleic acid linker is hybridized to a portion of the second single-stranded nucleic acid linker thereby forming the partially double-stranded nucleic acid linker linking the substrate to the oligonucleotide-based fluorescent label;

wherein the double-stranded segment of the linker comprises at least two polyA sequences and at least two polyC sequences in one strand and at least two polyT sequences and at least two polyG sequences in the other strand;

wherein the substrate linked to the oligonucleotide-based fluorescent label has a degree-of-labeling (DoL) of 1; and wherein there is no exchange of the substrate and the oligonucleotide-based fluorescent label in solution.

2. The fluorescently labeled bioconjugate of claim 1, wherein the partially double-stranded nucleic acid linker comprises from about 30 complementary base pairs to about 40 complementary base pairs.

3. The fluorescently labeled bioconjugate of claim 1, wherein the binding molecule is an antibody or an antigen-binding fragment, variant or derivative thereof, a peptide, a recombinant, natural or engineered receptor/ligand protein, an aptamer, a tetramer, a non-antibody protein or an antibody mimetic.

4. The fluorescently labeled bioconjugate of claim 1,
wherein the degree-of-labeling (DoL) of the substrate is
controlled stoichiometrically via the availability of the
first single-stranded nucleic acid linker.

5. The fluorescently labeled bioconjugate of claim 1,
wherein the bioconjugate can be used to specifically label a
cell, tissue, or organ for one or more of flow cytometry,
antibody screening, ELISA or other sandwich assays,
immune monitoring, biomarker assays, lateral flow, point-
of-care or rapid diagnostics, imaging, microscopy, molecu-
lar diagnostics, next generation sequencing, long read
sequencing, in situ sequencing, polymerase chain reaction,
microarrays, nucleic acid sequencing, amino acid sequenc-
ing, digital pathology, Southern blotting, Northern blotting,
or Western blotting.

6. A method of labeling a cell, tissue, or organ, the method
comprising:

contacting the cell, tissue, or organ with the fluorescently
labeled bioconjugate of claim 1, wherein the substrate
portion of the bioconjugate binds to an antigen, epitope,
or hapten of the cell, tissue, or organ.

7. The method of claim 6, wherein the labeled cell can be
used for one or more of flow cytometry, antibody screening,
ELISA or other sandwich assays, immune monitoring, bio-
marker assays, lateral flow, point-of-care or rapid diagnos-
tics, imaging, microscopy, molecular diagnostics, next gen-
eration sequencing, long read sequencing, in situ
sequencing, polymerase chain reaction, microarrays, nucleic
acid sequencing, amino acid sequencing, digital pathology,
Southern blotting, Northern blotting, Western blotting, or as
a reference sample.

8. A kit comprising:

(a) the fluorescently labeled bioconjugate of claim 1; and (b) instructions for use.

9. The kit of claim 8, wherein the kit further comprises
one or more of the following:

instructions either printed or on an electronic storage
medium, buffers, additional reagents, or packaging
materials.

\* \* \* \* \*

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
aaaaaaaaaa aaaaaaaaaa a                                              21

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
tttttttttt tttttttt                                                 18

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
tttttttttt ttttttttt t                                              21

<210> SEQ ID NO 4
<211> LENGTH: 18
<212> TYPE: DNA
```

-continued

```
<213> ORGANISM: Artificial Sequence
<220> FEATURE:
<223> OTHER INFORMATION: Synthetic

<400> SEQUENCE: 4
aaaaaaaaaa aaaaaaaa                                                    18

<210> SEQ ID NO 5
<211> LENGTH: 17
<212> TYPE: DNA
<213> ORGANISM: Artificial Sequence
<220> FEATURE:
<223> OTHER INFORMATION: Synthetic

<400> SEQUENCE: 5
tttttttttt ttttttt                                                     17

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
aaaaaaaaaa aaaaaaaaa a                                                 21

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
tttttttttt ttttttttt                                                   19

<210> SEQ ID NO 8
<211> LENGTH: 16
<212> TYPE: DNA
<213> ORGANISM: Artificial Sequence
<220> FEATURE:
<223> OTHER INFORMATION: Synthetic

<400> SEQUENCE: 8
tttttttttt tttttt                                                      16
```